(12) United States Patent
Weber et al.

(10) Patent No.: US 8,053,477 B2
(45) Date of Patent: Nov. 8, 2011

(54) INHIBITORS OF THE S100-P53 PROTEIN-PROTEIN INTERACTION AND METHOD OF INHIBITING CANCER EMPLOYING THE SAME

(75) Inventors: David J. Weber, Towson, MD (US); Joseph Markowitz, Baltimore, MD (US); France Carrier, Silver Spring, MD (US); Alexander D. MacKerell, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 685 days.

(21) Appl. No.: 10/397,239

(22) Filed: Mar. 27, 2003

(65) Prior Publication Data

US 2003/0219718 A1    Nov. 27, 2003

Related U.S. Application Data

(60) Provisional application No. 60/368,835, filed on Mar. 29, 2002.

(51) Int. Cl.
| | |
|---|---|
| A01N 37/52 | (2006.01) |
| A01N 31/14 | (2006.01) |
| A61K 31/155 | (2006.01) |
| A61K 31/075 | (2006.01) |
| G01N 33/53 | (2006.01) |

(52) U.S. Cl. ............ 514/636; 514/718; 435/7.1
(58) Field of Classification Search ........... 514/718, 514/634; 435/7.1
See application file for complete search history.

(56) References Cited

U.S. PATENT DOCUMENTS

| 6,693,125 B2 * | 2/2004 | Borisy et al. ............ 514/388 |
| 2002/0165261 A1 * | 11/2002 | Borisy et al. ............ 514/394 |

FOREIGN PATENT DOCUMENTS

| WO | WO 92/08464 | 5/1992 |
| WO | WO 00/45165 | 8/2000 |
| WO | WO 01/35935 | 5/2001 |

OTHER PUBLICATIONS

Cecil Textbook of Medicine, 21st Edition (2000), Goldman & Bennett (Editors), W.B. Saunders Company (Publisher), Chapter 198, pp. 1060-1074.*
Stedman's Medical Dictionary, 2nd Edition (electronic version), 2000, Lippincott Williams & Wilkins, <<http://www.thomsonhc.com/pdrel/librarian>>; retrieved via the PTO NPL website on Aug. 24, 2005.*
Jackel et al. "S-100-beta Protein im Serum als Tumormarker beim malignen Melanom". Hautarzt. 50, 1999:250-256. [English Abstract at p. 251].*
Nastruzzi et al. "Effects of Benzamidine Derivatives on Ha-ras-1 mRNA Accumulation in a Chinese Hamster Cell Line Transformed with the Activated Human T24 Ha-ras-1 Oncogene". Anticancer Research. 8, 1988:269-273.*
Bornstein et al. "An Evaluation of the Mechanism of Action of Pentamidine Isethionate". Journal of Surgical Oncology. 2(4), 1970:393-398.*
Bartolazzi et al. "Antitumor Activity of the Proteinase Inhibitor Tetra-p-amidinophenoxyneopentane in a Nude Mouse Model of Human Melanoma." In Vivo. 3, 1989:383-387.*
Nastruzzi et al. "Inhibition of 'in vitro' Tumor Cell Growth by Aromatic Polyamidines Exhibiting Antiproteinase Activity". Clin. Expl. Metastasis. 7(1), 1989:25-39.*
Lin et al. "Inhibition of p53 Transcriptional Activity by the S100B Calcium-Binding Protein". Journal of Biological Chemistry, 276(37); 2001:35037-35041.*
Pathak et al, *Mol. Cancer Therapeutics*, 1:1255-1264 (2002).
Jenkins et al, *Eur. J. Biochem.*, 213:1175-1184 (1993).
Barrett et al, *Parasitoloty*, 16(1):7-9 (2000).
Kopac, "Section of Biology", *The New York Academy of Science*, pp. 5-10 (Oct. 8, 1945).
Bailly et al, *Biochem. J.*, 323:23-31 (1997).
Nandi et al, *J. Indian. Chem. Sci.*, 70:527-531 (1993).
O'Conner et al, *Cancer Res.*, 57:4285-4300 (1997).
Perez et al, *Chem. Biol.* Interactions, 77:341-355 (1991).
Perez et al, *Chemio-Biol. Interactions*, 89:61-72 (1993).
Donato, R. "Functional roles of S100 proteins, calcium-binding proteins of the EF-hand type" Biochimica ET Biophysica Acta. Molecular Cell Research, Elsevier Science Publishers, Amsterdam, NL, vol. 1450, No. 3, Jul. 8, 1999, pp. 191-231.
Jing Lin et al. "Inhibition of p53 transcriptional activity by S100B calcium-binding protein" The Journal of Biological Chemistry, vol. 276, No. 37, Sep. 14, 2001, pp. 35037-35041.
Supplemental European Search Report for European Patent Application No. 03723795.5, Issue Date: Dec. 11, 2007.

* cited by examiner

*Primary Examiner* — Leslie A. Royds Draper
(74) *Attorney, Agent, or Firm* — Morgan, Lewis & Bockius, LLP

(57) ABSTRACT

Compounds that bind S100 and inhibit the S100-p53 protein-protein interaction and activate the tumor suppressor activity of p53, and thus which have an antineoplastic effect are disclosed, as well as methods for identifying these compounds, compositions comprising the same, and methods of using the same to treat cancer.

6 Claims, 17 Drawing Sheets

FIGURE 7

| | | | | |
|---|---|---|---|---|
| p53 consensus | 5'-Pu-Pu-Pu-C-A/T-T/A-G-Py-Py-Py-3' | 0 to 13 nt | 5'-Pu-Pu-Pu-C-A/T-T/A-G-Py-Py-Py-3' | |
| S100B 1705-1735 | 5' G G G C A A G C T C | 11 nt | G A G C A A G C C T 3' | |
| MDM2 RE1 | 5' G G t C A A G T T C | 0 nt | A G A C A c G T T C 3' | |
| GADD45 +1569 | 5' G A A C A T G T C T | 0 nt | A A G C A T G C T g 3' | |
| S100A2 -3811 | 5' G G G C A T G T g T | | G G G C A c G T T C 3' | |

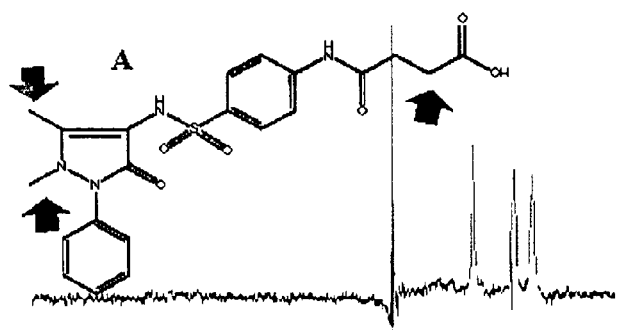
FIGURE 14A
FIGURE 14B
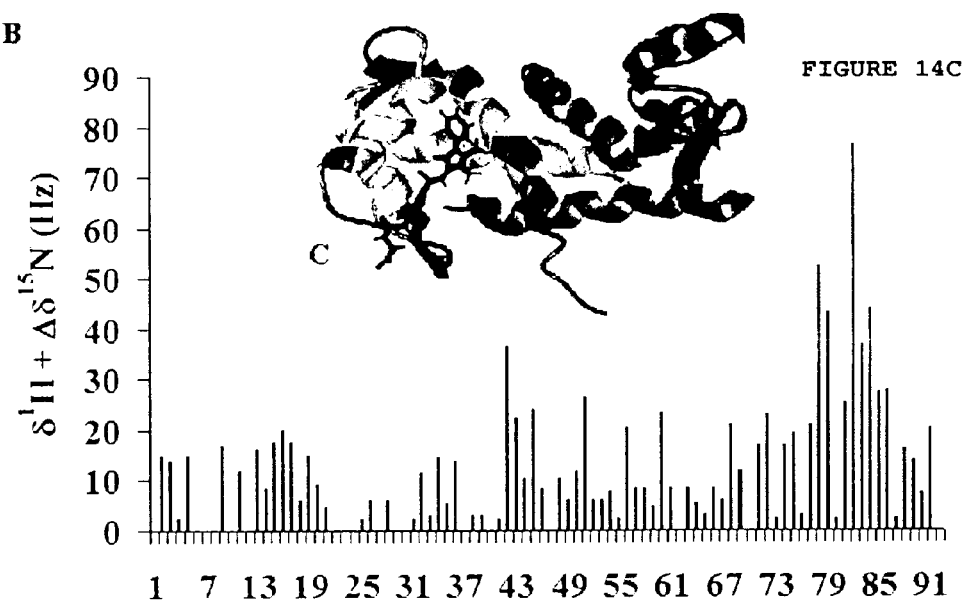
FIGURE 14C
FIGURE 14D n
4 1a
5 1b
6 1c
7 1d
8 1e n
4 2a
5 2b
6 2c
7 2d
8 2e n
4 3a
5 3b
6 3c
7 3d
8 3e

```
                         SEQUENCE LISTING

<160> NUMBER OF SEQ IDS NOS: 5

<210> SEQ ID NO 1
<211> LENGTH: 22
<212> TYPE: PRT
<213> ORGANISM: Homo sapiens

<400> SEQUENCE: 1

Ser His Leu Lys Ser Lys Lys Gly Gln Ser Thr Ser Arg His Lys Lys
1               5                   10                  15

Leu Met Trp Lys Thr Glu
            20

<210> SEQ ID NO 2
<211> LENGTH: 11
<212> TYPE: PRT
<213> ORGANISM: Homo sapiens

<400> SEQUENCE: 2

Thr Arg Thr Lys Ile Asp Trp Asn Lys Ile Leu
1               5                   10

<210> SEQ ID NO 3
<211> LENGTH: 39
<212> TYPE: DNA
<213> ORGANISM: Homo sapiens

<400> SEQUENCE: 3
gcctgggcaa gctctgtgct tcacagagca agcctgtgt                            39

<210> SEQ ID NO 4
<211> LENGTH: 33
<212> TYPE: DNA
<213> ORGANISM: Homo sapiens

<400> SEQUENCE: 4
gttctgggac tttcactaaa cttctcctac cat                                  33

<210> SEQ ID NO 5
<211> LENGTH: 33
<212> TYPE: DNA
<213> ORGANISM: Homo sapiens

<400> SEQUENCE: 5
cagagggcag gcccggctgg gccctcctgc tga                                  33
```

INHIBITORS OF THE S100-P53 PROTEIN-PROTEIN INTERACTION AND METHOD OF INHIBITING CANCER EMPLOYING THE SAME

CROSS-REFERENCE TO RELATED APPLICATIONS

This application claims benefit under 35 U.S.C. §119(e)(1) of Provisional Application Ser. No. 60/368,835 filed Mar. 29, 2002, the disclosure of which is incorporated by reference herein in its entirety.

The work described herein was supported by grants from the NIH (grant numbers GM58888, NSO43916 and GM052071) and from the American Cancer Society (RPG0004001-CCG). The Federal Government has certain rights in this invention.

FIELD OF THE INVENTION

The present invention relates, e.g., to small molecule compounds that bind S100 and inhibit the S100-p53 interaction and activate the tumor suppressor activity of p53, and thus which have an antineoplastic effect, and to methods of identifying these compounds by, e.g., assaying for inhibition of p53 binding to S100, compositions comprising these compounds, and methods of using the same to treat melanoma and other cancers.

BACKGROUND OF THE INVENTION

I. The S100 Proteins

There are now more than 20 members of the S100 family of EF-hand $Ca^{2+}$-binding proteins, which are known to be widely distributed in human tissue (Zimmer et al, *Brain Res. Bull.*, 37:417-429 (1995); Donato, *Int. J. Biochem. Cell. Biol.*, 33:637-668 (2001); and Heizmann et al, *Frontiers in Bioscience* 7:1356-1368 (2002)). S100 proteins were given this name because they are soluble in 100% saturated ammonium sulfate (Moore, *Biochem. Biophys. Res. Comm.*, 19:739-744 (1965)). One member, S100B, is a 21.5 kDa symmetric homodimer that is highly conserved (>95%) among mammals (Zimmer et al, supra; and Moore, supra). In a manner similar to calmodulin, a $Ca^{2+}$-dependent conformational change is required for S100B to bind a target protein (FIG. 1; Rustandi et al, *Nat. Struct. Biol.*, 7:570-574 (2000); Rustandi et al, *Biochem.*, 37:1951-1960 (1998); Weber et al, "Interaction of Dimeric S100B(ββ) with the Tumor Suppressor Protein: A Model for $Ca^{2+}$-dependent S100-Target Protein Interactions", The Molecular Basis of Calcium Action in Biology and Medicine (Pochet, R., Ed.), Kluwer Academic Publishers, Dordrecht, The Netherlands (2000); and Kligman et al, *Trends Biochem. Sci.*, 13:437-443 (1988)).

In general, low levels of S100B have trophic effects, and higher levels are toxic, resulting in uncontrolled cell growth (Castets et al, *Brain Res.*, 46:208-216 (1997); Van Eldik et al, *Biochimica et Biophysica Acta*, 1223:398-403 (1994); Mariggio et al, *Neuroscience*, 60:29-35 (1994); and McLendon et al, In: *Cancer diagnosis in vitro using monoclonal antibodies* (Kubchik, H. Z., ed) Vol. 39, pp. 31-66, Marcel Dekker, New York (1988). Increased levels of S100B are found in renal cell tumors (Takashi et al., *Urol. Res.*, 22:251-255 (1994)), and malignant mature T-cells (such as doubly negative CD4$^-$/CD8$^-$ adult T-cells in leukemia patients) (Suzushima et al, *Leuk. Lymph.*, 13:257-262 (1994)). Furthermore, S100B is up regulated by other cytokines that stimulate gliosis, such as interleukin-1β and the basic fibroblast growth factor (Hinkle et al, *Neuroscience*, 82:33-41 (1998)).

As is the case for S100B, a number of other S100 proteins are regulated in a tissue-specific manner (Kligman et al, supra). S100A1, calcyclin (S100A6), and S100B levels are elevated significantly in metastatic human mammary epithelial cells (Pedrocchi et al, *Int. J. Cancer*, 57:684-690 (1994)), and increased levels of S100A4 mouse (mts1) in transgenic mice induce metastatic mammary tumors (Chen et al, *J. Biol. Chem.*, 272:20283-20290 (1997)). In the case of mts1, protein levels are controlled in benign cell lines via a cis-acting element 1300 base pairs upstream of the rat mts1 start site (Chen et al, supra), and expression of antisense RNA to mts1 suppresses metastatic potential for a high-metastatic Lewis lung carcinoma (Takenaga et al, *Oncogene*, 14:331-337 (1997)). Protein levels of S100B, mts1, and calcyclin correlate with malignant melanoma. Thus, S100 proteins are used as markers for this cancer (Maelandsmo et al, *Int. J. Cancer*, 74:464-469 (1997); Boni et al, *J. Cutan. Pathol.*, 24:76-80 (1997); Xia et al, *Cancer Res.*, 57:3055-3062 (1997); Hansson et al, *Anticancer Res.*, 17:3071-3073 (1997); and FIG. 2B).

S100 antibodies are used clinically to identify and classify malignant tumors in several tissues including brain, lung, bladder, intestine, kidney, cervix, breast, skin, head and neck, lymph, testes, larynx, and mouth among others (Takashi et al, supra; Suzushima et al, supra; Pedrocchie et al, supra; Fisher et al, *J. Clin. Path.*, 47:868-869 (1994); Iniue et al, *J. Urol.*, 85:495-503 (1994); Kerrebijn et al, *Cancer Immun. Immunother.*, 38:31-37 (1994); Colasante et al, *Am. Rev. Resp. Dis.*, 148:752-759 (1993); Zeid et al, *Path.*, 25:338-343 (1993); Gallo et al, *Arch. Otolarn.*, 117:1001-1010 (1991); Wilson et al, *J. Path.*, 163:25-30 (1991); Lee et al; *Proc. Natl. Acad. Sci. USA*, 89:2504-2508 (1992); Leong et al, *J. Path.*, 162:35-41 (1990); Nakano et al, *Arch. Path. Lab. Med.*, 113:507-511 (1989); Kurihara et al, *J. Oral. Path.*, 14:289-298 (1985); Matsushima et al, *J. Surg. Onc.*, 55:108-113 (1994); Renshaw et al, *Mod. Path.*, 10:693-700 (1997); Larock et al, *Vet. Path.*, 34:303-311 (1997); and Hurley et al, *J. Med. Primat.*, 26:172-180 (1997)).

II. p53 p53 is a transcription activator that signals for cell cycle arrest and apoptosis and plays a pivotal role in the maintenance and regulation of normal cellular functions (Levine et al, *Nature*, 351:453-456 (1991); and Levine, *Cell*, 88:323-331 (1997)). The inactivation of p53 affects cell cycle checkpoints, apoptosis, gene amplification, centrosome duplication and ploidy (Levine (1997), supra; Woods et al, *Exp. Cell. Res.*, 264:56-66 (2001); Burns et al, *J. Cell. Physiol.*, 181: 231-239 (2001); Appella et al, *Eur. J. Biochem.*, 268:2764-2772 (2001); Arrowsmith et al, *Cell Death Differ.*, 6:1169-1173 (1999); Prives et al, *J. Pathol.*, 187:112-126 (1999); Vousden, *Cell*, 103:691-694 (2000); and Ryan et al, *Curr. Opin. Cell. Biol.*, 13:332-337 (2001)). If p53 is inactivated by mutation, as found in over 50% of human cancers, the cell cycle proceeds unregulated and cell growth proliferates. Likewise, apoptosis pathways are not induced, and proliferating cells transform into cancerous ones (Woods et al, supra; Burns, supra; Appella et al, supra; Arrowsmith et al, supra; Prives et al (1999), supra; Vousden, supra; Ryan et al, supra; and Agarwal et al, *J. Biol. Chem.*, 273:1-4 (1998)). On the other hand, if p53 levels are too high, then problems associated with aging occur (Tyner et al, *Nature*, 415:45-53 (2002)). p53 is highly regulated by post-translational modifications and by interactions with other proteins inside the cell (Appella et al, supra; Minamoto et al, *Oncogene*, 20:3341-3347 (2001); Jayaraman et al, *Cell. Mol. Life Sci.*, 55:76-87 (1999);

Jimenez et al, *Oncogene* 18:7656-7665 (1999); and Meek, *Pathol. Biol.*, 45:804-814 (1997)).

III. The S100-p53 Interaction

S100B and several other S100 proteins (i.e., S100A1 and mts1) interact with the tumor suppressor protein, p53, in cancer cells resulting in significantly reduced p53 levels, and p53-dependent transcription activation of target genes is inhibited (Grigorian et al, *J. Biol. Chem.*, 276:22699-22708 (2001); Lin et al, *J. Biol. Chem.*, 276:35037-35041 (2001); and Carrier et al, *Proc. AACR*, 40:102 (1999)).

The interactions between the C-terminus of p53 and S100 calcium binding proteins, such as S100B are of particular interest since like p53, S100 proteins affect cell cycle progression, are over expressed in numerous tumor cells, and are associated with tumor progression (Ilg et al, *Int. J. Cancer*, 68:325-332 (1996)). These results correlate with knowledge that p53 and S100B (i) interact tightly in vitro ($K_D$=24±10 nM; Delphin et al, *J. Biol. Chem.*, 274:10539-10544 (1999)), (ii) S100B inhibits PKC-dependent phosphorylation of p53 (Wilder et al, *Protein Sci.*, 7:794-798 (1998); and Baudier et al, *Proc. Natl. Acad. Sci., USA*, 89:11627-11631 (1992)), (iii) S100B dissociates the p53 tetramer (Baudier et al, supra), (iv) subunits of both S100B and the C-terminus of p53 associate via an X-type four-helix bundle structural motif (Weber et al, supra; Jeffrey et al, supra; and Lee et al, supra); and (v) three S100 proteins (S100B, S100A1, mts1) inhibit p53 function in vivo (Grigorian et al, supra; Lin et al, supra; and Carrier et al (1999), supra).

In the present invention it is demonstrated that in primary malignant melanoma cancer cells, S100B interacts directly with p53 in a cell-cycle dependent manner resulting in lower levels of wild-type p53. In addition, it was found in the present invention that the S100B promoter has three sequences that bind to p53, which supports the notion that S100B transcription, in turn, is regulated by p53 in a feed back loop that triggers p53's own degradation.

DETAILED DESCRIPTION OF THE DRAWINGS

FIG. 1 illustrates the $Ca^{2+}$-dependent interaction of S100B with the C-terminus (amino acids 367-388) of the tumor suppressor protein, p53 (target protein). Ribbon diagrams are illustrated for the atomic resolution three-dimensional solution structures of S100B in the apo-, calcium-bound (holo-), and p53-bound states (PDB entries: apo-S100B; holo-S100B, 1B4C; p53-bound S100B, 1DT7). Shown in red and blue are subunits of dimeric S100B with regions shaded (yellow) for residues that interact directly with the C-terminal negative regulatory domain (residues 367-388) of the tumor suppressor protein, p53 (green). A large conformational change occurs upon the addition of calcium to apo-S100B. This conformational change exposes residues (colored yellow) involved in binding p53 (green), and is required for binding of the tumor suppressor to holo-S100B (Rustandi et al (2000), supra; and Weber et al, supra).

FIGS. 2A-2B show Western blots of S100B (FIG. 2A) and p53 (FIG. 2B) in primary malignant melanoma cells (C8146) and in control cells with little or no S100B (glioblastomas, U118). Shown also are blots of recombinant S100B used to estimate the amount of S100B. This figure illustrates that melanoma has increased S100B levels and reduced p53 levels.

Figure 5A:
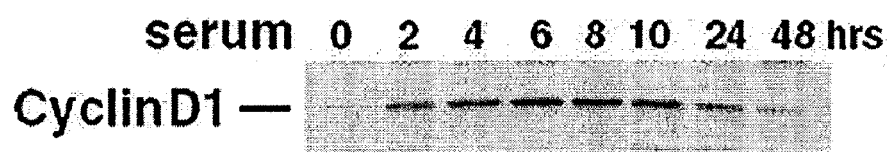
Figure 5B:
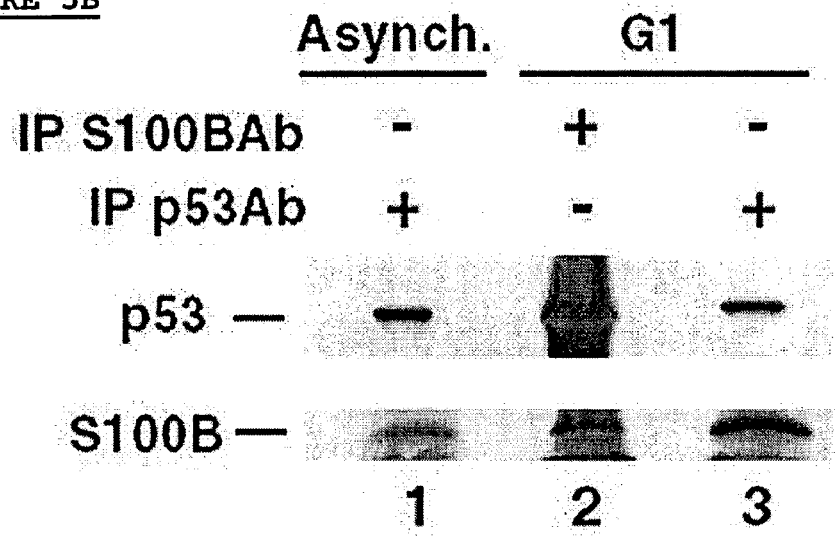

FIGS. 5A-5B show the interaction of S100B with p53 during $G_1$ of the cell cycle in primary malignant melanoma cancer cells as detected by co-immunoprecipitation experiments. FIG. 5A shows Western blot of the cell cycle protein, cyclin D1, used as a marker for $G_1$; and FIG. 5B shows co-immunoprecipitation with S100B and p53 antibodies. The interaction of S100B with p53 is minimal (if any) in asynchronized cells (FIG. 5B, lane 1), but is significantly increased when the cells are synchronized by serum starvation and released in $G_1$ 6 hrs after addition of 15% (v/v) serum (FIG. 5B; lanes 2, 3).

Figure 6A:
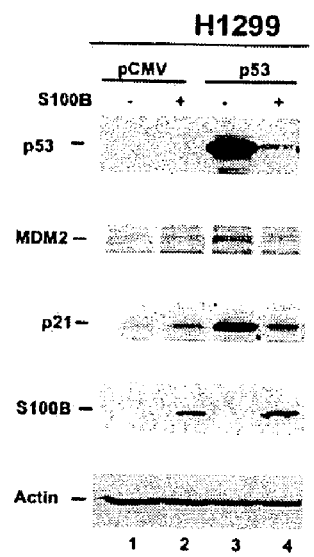
Figure 6B:
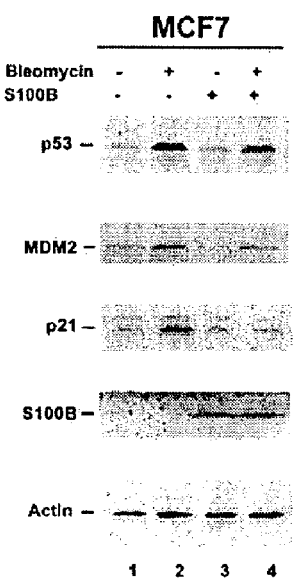

FIGS. 6A-6B shows that S100B decreases p53, mdm2 and p21 proteins levels. FIG. 6A shows Western blots of H1299 lung cancer cells transfected with p53 with (+) or without (−) S100B. FIG. 6B shows Western blots of breast cancer MCF-7 cells transiently transfected with S100B (+) or pCMV (−) and treated or not with 10 mg/ml bleomycin. The positions of the p53, mdm2, p21, S100B and the actin proteins are indicated. These results demonstrate that transient transfections of S100B inhibit p53 function in cancer cells.

FIG. 7 shows regions of the S100B promoter that match the p53 binding consensus sequence. The nucleotides 1705-1735 match 20 out of the 20 consensus nucleotides for p53 binding. Two additional p53 binding sites occur in the S100B promoter; the nucleotides 1455-1478 match 16 sites while the nucleotides 149-169 match 17 sites. The p53 binding regions in the mdm2 (18/20) and GADD45 (19/20) promoters are also shown. This figure illustrates that three p53 binding sites are in the S100B promoter.

Figure 8:
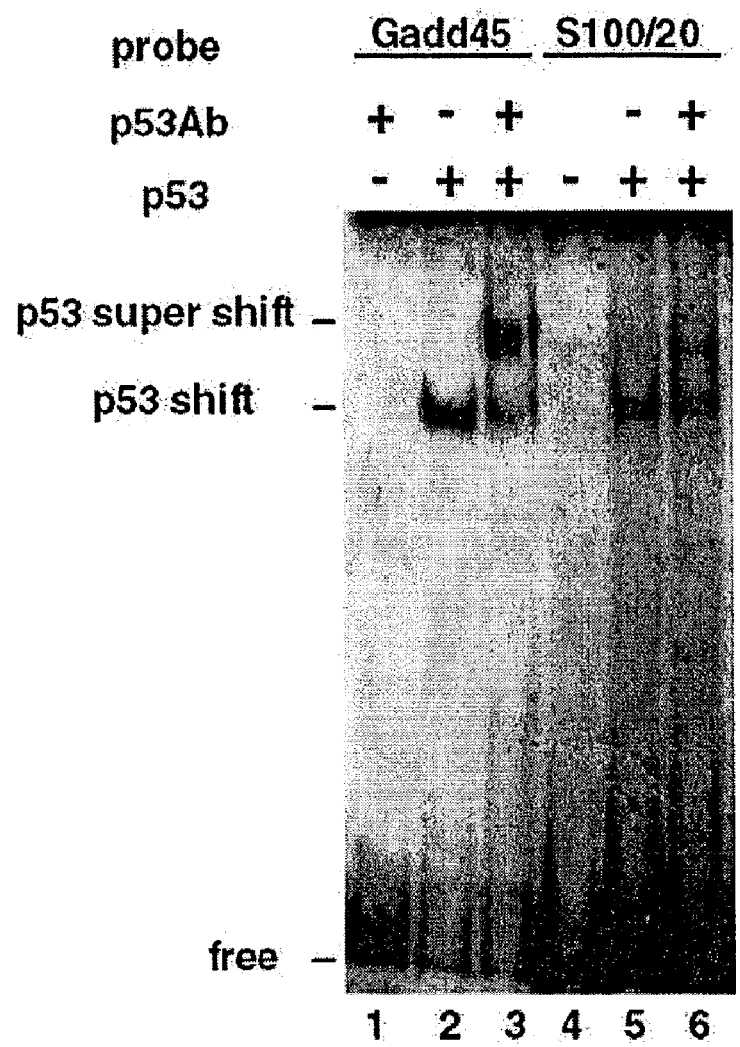

FIG. 8 shows the results of a mobility shift assay of purified p53 to DNA from the $3^{rd}$ intron of the GADD45 gene (lanes 1-3) and to DNA from the promoter of S100B (20/20 match) (lanes 4-6). The free probe, the p53 shift and super shifted bands are indicated. For GADD45 shift, 0.3 μg of purified p53 and 5.0 ng of labeled DNA were used, while 6.0 μg of p53 and 25 ng of S100B labeled DNA were used. These results indicate that p53 binds the S100B promoter and likely regulates S100B levels after genes such as GADD45. This is because p53 binds DNA from the $3^{rd}$ intron of the GADD45 gene at lower p53 and DNA levels than found for the DNA from the S100B promoter.

Figure 9:
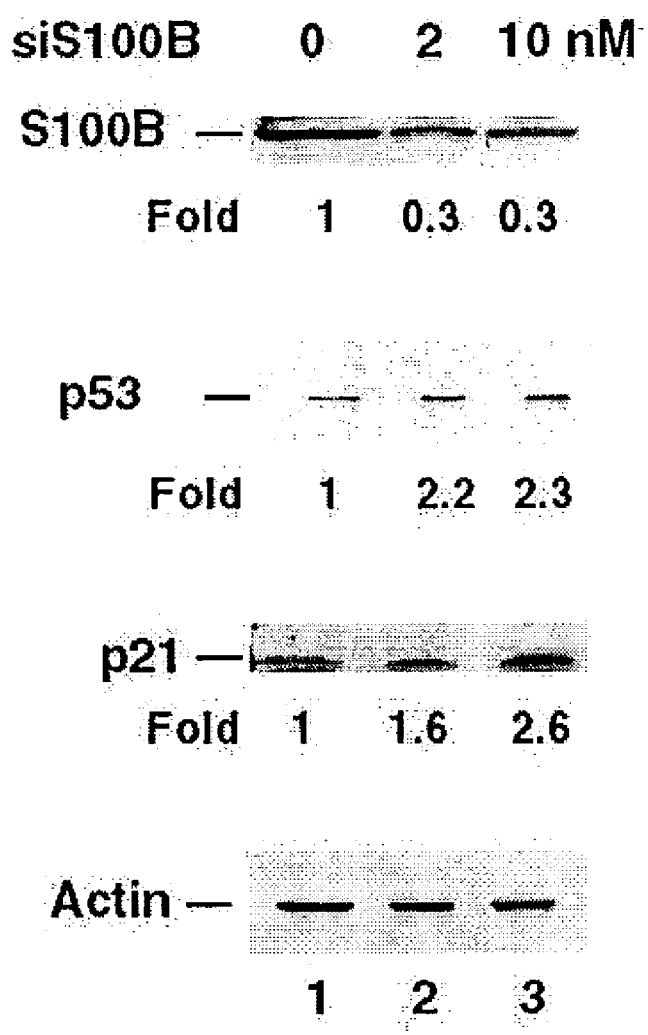

FIG. 9 shows Western blots analyses of p53, S100B, p21 and actin after transfection of melanoma cells with small interfering S100β antisense RNA (siS100β). S100β=subunit of dimeric S100B. The amounts of transfected RNA used are indicated. The cells were harvested 24 hrs after transfection. These results demonstrate that inhibiting S100B protein production in malignant melanoma cells restores wild-type p53 function. This experiment demonstrates a proof of principle for this invention.

Figure 10:
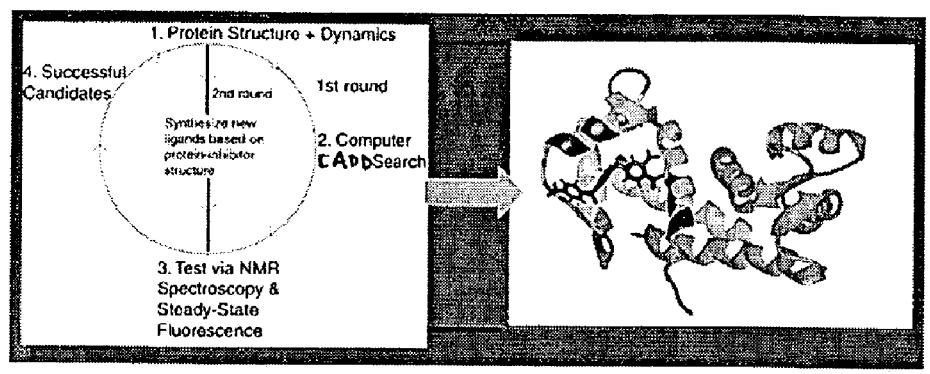

FIG. 10 shows a rational drug design of S100B using CADD and NMR-derived structural and dynamic data (left panel). In the present invention, the work from this approach has provided lead compounds (right panel; in blue) that bind S100B and inhibit the S100B-p53 interaction, as necessary for drug development.

Figure 11:
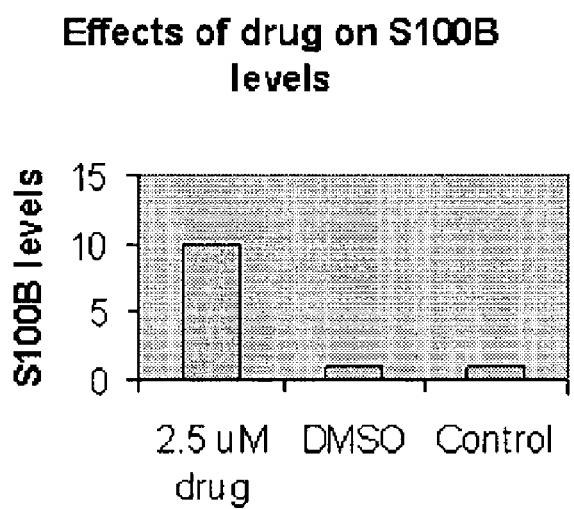
Figure 16:
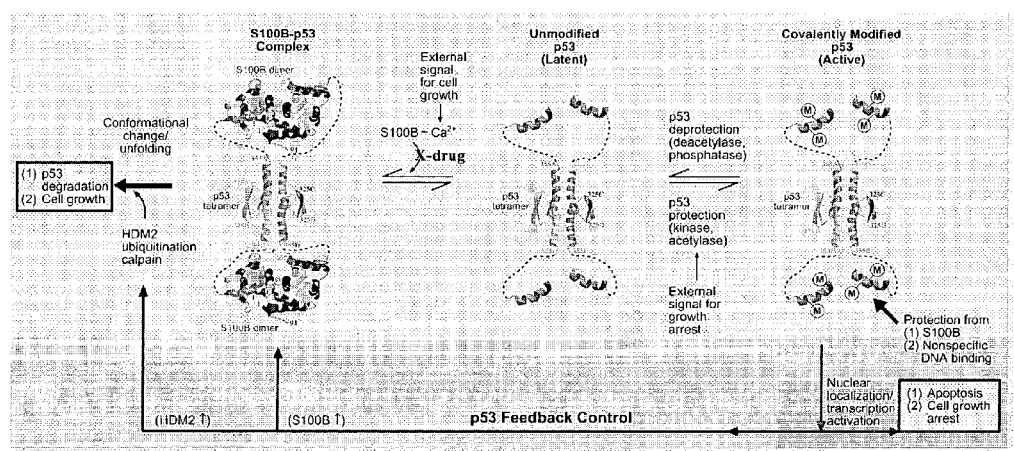

FIG. 11 shows that additions of the drug pentamidine (2.5 μM) increase S100B levels in human malignant melanoma cells relative to controls (1.0% (v/v) DMSO; and untreated). Wild-type p53 levels are restored by the drug via inhibiting the S100B-p53 interaction. Elevated p53 then up regulates S100B as part of a feedback mechanism (FIG. 16). This data illustrates that monitoring the elevation of S100B levels can be used as an assay for a particular drug's ability to restore p53 function.

Figure 12A:
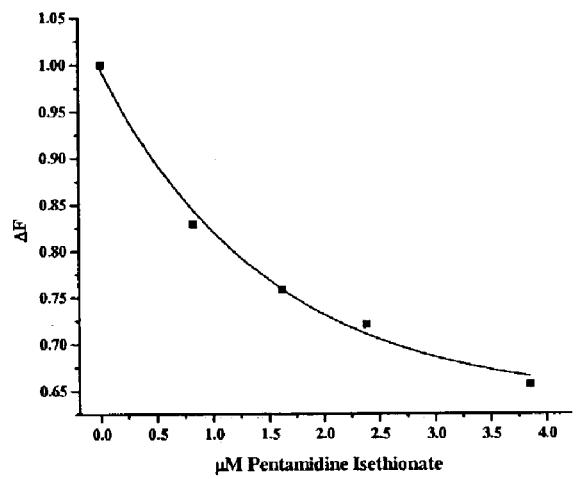
Figure 12B:
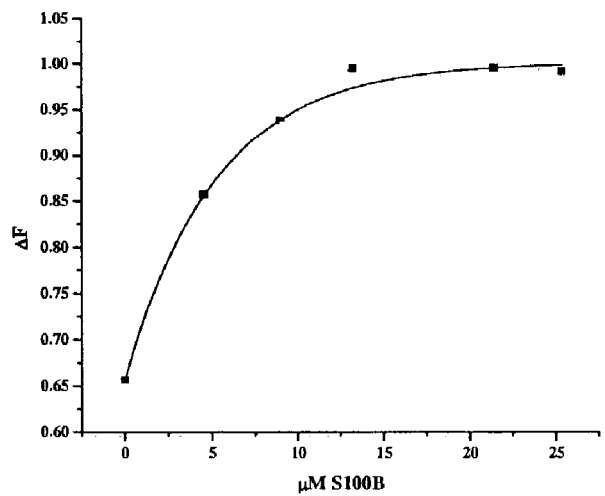

FIG. 12A-12B show binding studies of pentamidine isethionate to holo-S100B. FIG. 12A shows titration of pentamidine isethionate into a solution containing 4.0 μM F43W S100B, 10 mM $CaCl_2$, 40 mM Tris (pH 7.5). FIG. 12B shows competition studies of pentamidine bound to F43W S100B with wild-type S100B. In these titrations, the concentrations of S100B mutant, F43W, and pentamidine isethionate were kept constant throughout the titration. This competition study yielded a binding constant ($K_D$) between wild-type holo-S100B and pentamidine of 700 nM.

Figure 13:
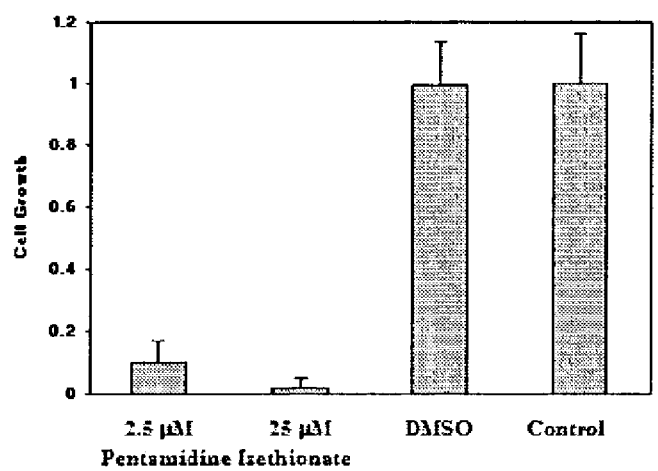

FIG. 13 shows the effects of pentamidine isethionate on the growth of primary malignant melanoma cells (C8146A). Compounds such as pentamidine isethionate were screened in quadruplicate trials using a primary melanoma cell line at 2 concentrations of drug (2.5 μM, 25 μM). The $IC_{50}$ for inhibition of cell growth by pentamidine was found to be approximately 500 nM. In contrast, a 7.5 fold lesser effect (at 25 μM drug) was found in growth in normal neonatal melanocytes. These data demonstrate that pentamidine isethoionate can inhibit primary malignant melanoma cell growth more efficiently than normal melanocytes.

FIGS. 14A-14D show mapping of the holo-S100B-compound-4 binding interface using NMR spectroscopy. FIG. 14A shows the structure of Compound 4 illustrating (bold arrows) those regions of the compound that interact with S100B as determined in saturation transfer difference (STD) NMR experiments. FIG. 14B shows STD data for Compound 4 binding to holo-S100B. Shown in black is the STD spectrum and shown in red is the control spectrum. FIG. 14C shows a ribbon diagram illustrating Compound 4 bound to holo-S100B as determined by STD experiments and chemical shift perturbation experiments. Shown in red on holo-S100B are residues that were found to have large changes in chemical shift upon the binding of Compound 4. FIG. 14D shows chemical shift changes for each residue in S100B illustrating the magnitude of the chemical shift change for each residue. Sample conditions for the NMR experiments consisted of 1.5 mM Compound 4, 0.150 mM $Ca^{2+}$-S100B, 10 mM $CaCl_2$, 30 mM Tris (pH 6.5), 5.0 mM DTT, 0.3 mM $NaN_3$, and 5.0% (v/v) $D_2O$. The structure of Compound 4 is shown below. These data illustrate the methods for characterizing the S100B-drug interaction at atomic resolution, as necessary for optimizing the S100B-drug interaction.

Figure 15:
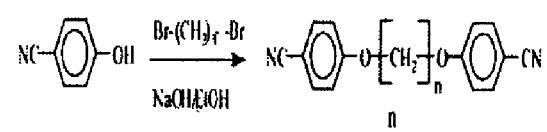
Figure 15:
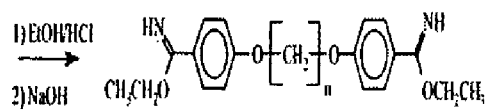
Figure 15:
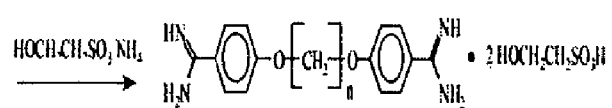

FIG. 15 shows a synthesis reaction for preparing derivatives of pentamidine with varying sized linker regions.

FIG. 16 shows a model for the activation and inactivation of wild-type p53. Activation of latent p53 is achieved by stress response-dependent covalent modifications (M) (i.e., phosphorylation, sumoylation, and acetylation). These modifications are believed to protect the C-terminal negative regulatory domain of p53 (green helices) and the p53 tetramer domain from S100 proteins and/or from nonspecific DNA binding. Activated p53 is localized to the nucleus where it up regulates the transcription of genes involved in apoptosis (i.e., bax) and cell cycle-dependent growth arrest (i.e., p21). As part of a feedback control mechanism, p53 also up regulates the transcription of genes involved in its own inactivation (i.e., hdm2 and S100B). As part of a growth response (↑$Ca^{2+}$), the $Ca^{2+}$-dependent interaction between S100B and p53 induces a conformational change in p53 and tetramer dissociation of the tumor suppressor, which contributes to its degradation (i.e., likely via hdm2/ubiquitin- and/or protease-dependent pathways).

Figure 17:
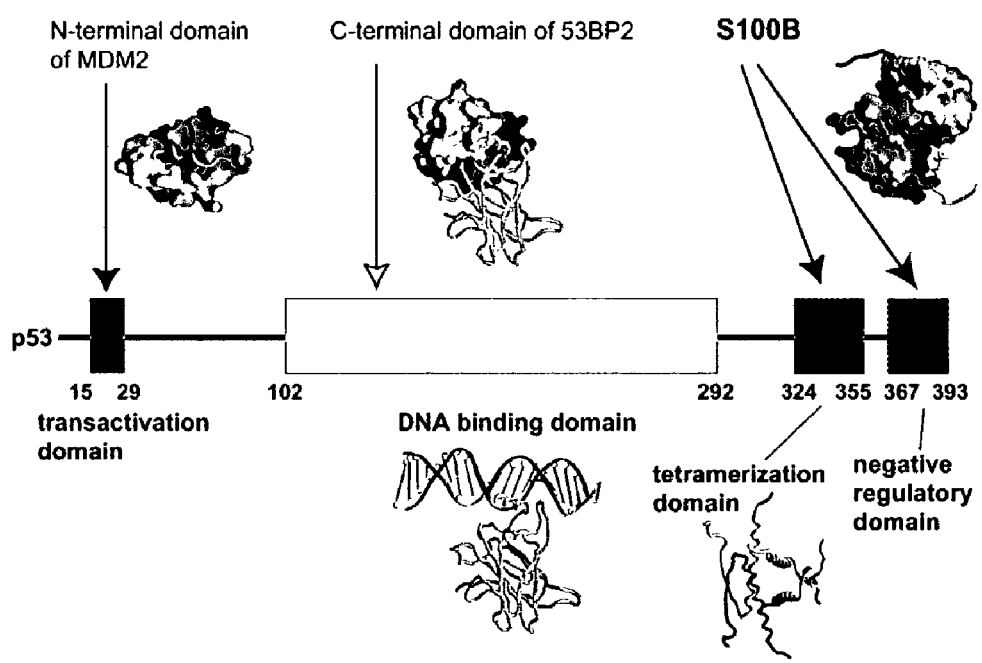

FIG. 17 shows the domains of p53, together with the color coded 3D structures as determined by x-ray crystallographs and/or by NMR (Ikura et al, *Nat. Struct. Biol.,* 7:525-527 (2000)). Structures of the p53 domains are either free in solution or bound to a p53 binding protein or DNA.

SUMMARY OF THE INVENTION

In one embodiment, the present invention relates to a method of identifying compounds that bind S100 proteins (e.g., S100B, S100A1 and S100A4) and prevent binding of inhibitory proteins, such as S100 proteins, to p53.

In another embodiment, the present invention relates to a method of identifying compounds that activate p53 by measuring p53 function, in particular overexpression of S100B and other S100 proteins, due to p53 activation.

In still another embodiment, the present invention relates to a method of using the identified compounds, including but hot limited to pentamidine and derivatives thereof to inhibit binding of S100B and other S100 proteins to p53, i.e., to activate p53.

In still another embodiment, this invention relates to a method of using the identified compounds, including but not limited to pentamidine and derivatives thereof to treat cancer.

Without wishing to be bound to any particular mechanism, it is believed that the compounds of the present invention, by interacting with S100B and other S100 proteins, particularly with the p53 binding domain thereof, prevent inactivation of p53, and thereby reduce or prevent neoplastic cell proliferation. Thus, the present invention relates, e.g., to compounds that activate p53, in particular compounds that interact specifically with members of the S100 protein family, more particularly to compounds that prevent the binding of S100 proteins, such as, S100B to p53.

These and additional objects of the present invention, which will be apparent from the detailed description of the present invention, have been met by a compound represented by formulae (I) to (XIII), or a pharmaceutically acceptable salt thereof, as herein defined and their use.

DETAILED DESCRIPTION OF THE INVENTION

As discussed above, in one embodiment, the present invention relates to a method of identifying compounds that prevent binding of inhibitory proteins, such as S100B and other S100 proteins, to p53.

In another embodiment, the present invention relates to a method of identifying compounds that activate p53 by measuring p53 function, in particular overexpression of S100 due to p53 activation.

In still another embodiment, the present invention relates to a method of using the identified compounds to activate p53.

In still another embodiment, this invention relates to a method of using the identified compounds to treat cancer.

It has been found in the present invention that pentamidine inhibits the S100-p53 interaction. Because pentamidine is active, and is an FDA approved drug (for another use), the present invention also relates to pentamidine derivatives with increased binding affinity to S100. Thus, the compounds of the present invention are represented by formulae (I) to (XIII), or a pharmaceutically acceptable salt thereof, below:

Formula (I):

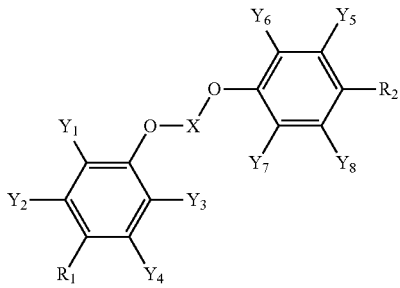

wherein $Y_1, Y_2, Y_3, Y_4, Y_5, Y_6, Y_7$, and $Y_8$ are each independently selected from the group consisting of hydrogen, methyl, ethyl, propyl, isopropyl, halogen, methyl ether, methyl ketone, and methyl ester;

X is an alkyl having 1 to 8 carbon atoms;

$R_1$ and $R_2$ which may be the same or different are selected from the group consisting of 1-3 adjacent amidines, 1-3 adjacent amines, 1-3 adjacent guanidines, amide, urea, carbamide, carbonate, carboxylate, anhydride, thioamide, thiourea, thiocarbamide, thiocarbonate, thioanhydride, hydroxyl, an ester (e.g., an alkyl ester, acyl ester, aryl ester, alkyl thioester, acyl thioester, or aryl thioester), and $CZ_nH_{3-n}$, where Z is a halogen, and n is 1 to 3, e.g., pentamidine:

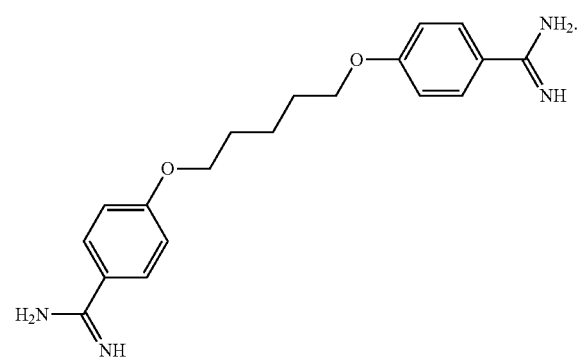

Formula (II):

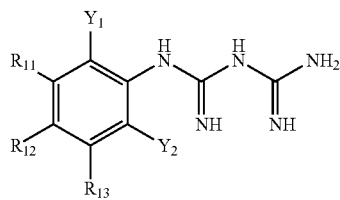

wherein $Y_1$ and $Y_2$ are each independently selected from the group consisting of hydrogen, methyl, ethyl, propyl, isopropyl, halogen, methyl ether, methyl ketone, and methyl ester;

$R_{11}, R_{12}$, and $R_{13}$ are each independently selected from the group consisting of hydrogen, methyl, ethyl, propyl, isopropyl, halogen, methyl ether, methyl ketone, methyl ester, phenyl ketone, aryl ether, aryl thio, aryl methylene, oxygen, carbonyl, carboxylate, ethylene, amide, ester, thioester, and $CZ_nH_{3-n}$ where Z is halogen and n is 1 to 3, wherein optionally $R_{11}$ and $R_{12}$, or $R_{12}$ and $R_{13}$ may form a 5-membered fused aromatic ring comprising C, N, O, or S, e.g., {[(2,3,dichloroanilino)(imino)methyl]amino} methanimidamide (Compound 3):

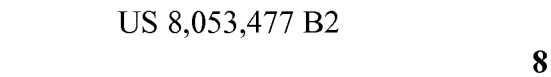

Formula (III):

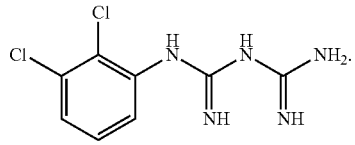

wherein $Y_1, Y_2, Y_3, Y_4, Y_5, Y_6, Y_7, Y_8$, and $Y_9$ are each independently selected from the group consisting of hydrogen, methyl, ethyl, propyl, isopropyl, halogen, methyl ether, methyl ketone, and methyl ester;

$X_2$ is selected from the group consisting of sulfur, $SO_2$, SO, $NHSO_2$, methylene, oxygen, carbonyl, imine, ethylene, amide, ester and thioester, wherein one or more of the phenyl aromatic rings may be replaced by a fused aromatic ring, heteroaromatic ring, or fused heteromatic ring, by replacing 1-3 carbon atoms of one of more of the aromatic rings with N atoms (e.g., naphthyl, pyridinyl, quinolinyl, and isoquinolinyl rings), e.g., {[(2-benzoyl-4-chloroanilino)(imino)methyl]amino} methanimidamide (Compound 9):

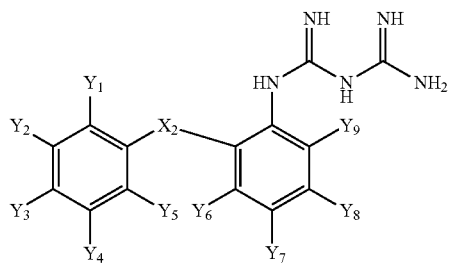

Formula (IV):

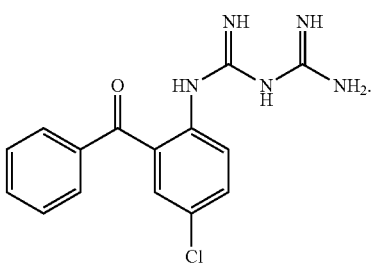

wherein $Y_1, Y_2, Y_3, Y_4, Y_5, Y_6$, and $Y_7$ are each independently selected from the group consisting of hydrogen, methyl, ethyl, propyl, isopropyl, halogen, methyl ether, methyl ketone and methyl ester;

$R_1$ is selected from the group consisting of 1-3 adjacent amidines, 1-3 adjacent amines, 1-3 adjacent guanidines, amide, urea, carbamide, carbonate, carboxylate, anhydride, thioamide, thiourea, thiocarbamide, thiocarbonate, thioanhydride, hydroxyl, an ester (e.g., an alkyl ester, acyl ester, aryl ester, alkyl thioester, acyl thioester, or aryl thioester), and $CZ_nH_{3-n}$ where Z is a halogen, and n is 1 to 3;

$R_{15}$ is a nitrogen or NO;

$R_{16}$ is a negatively charged functional group (e.g., $NO_2$, or $SO_2$), e.g., 2-[2-(3-nitrophenyl)-2-oxoethoxy]-5-(tri-fluoromethyl)pyridinium-1-olate (Compound 1):

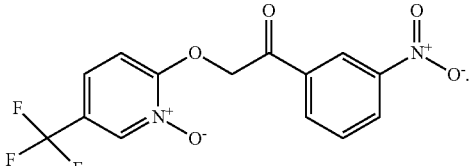

Formula (V):

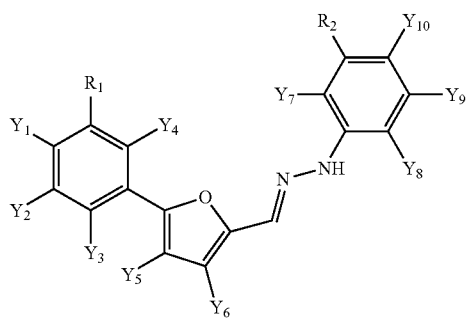

wherein $Y_1, Y_2, Y_3, Y_4, Y_5, Y_6, Y_7, Y_8, Y_9,$ and $Y_{10}$ are each independently selected from the group consisting of hydrogen, methyl, ethyl, propyl, isopropyl, halogen, methyl ether, methyl ketone, and methyl ester;

$R_1$ and $R_2$ which maybe the same or different are selected from the group consisting of 1-3 adjacent amidines, 1-3 adjacent amines, 1-3 adjacent guanidines, amide, urea, carbamide, carbonate, carboxylate, anhydride, thioamide, thiourea, thiocarbamide, thiocarbonate, thioanhydride, hydroxyl, an ester (e.g., an alkyl ester, acyl ester, aryl ester, alkyl thioester, acyl thioester, or aryl thioester), and $CZ_nH_{3-n}$ where Z is a halogen, and n is 1 to 3, e.g., 2-Chloro-5-[N'(5-(3-chloro-4-benzoic)-furan-2ylmethylene-hydrazino]-benzoic acid (Compound 31):

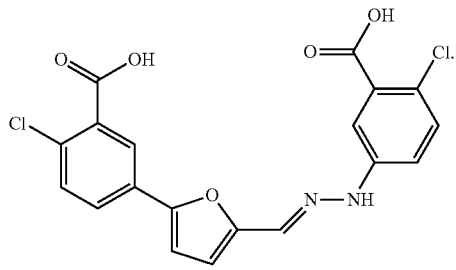

Formula (VI):

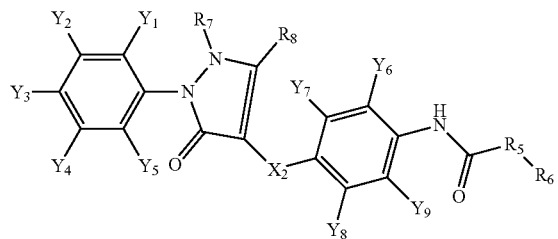

wherein $Y_1, Y_2, Y_3, Y_4, Y_5, Y_6, Y_7, Y_8,$ and $Y_9$ are each independently selected from the group consisting of hydrogen, methyl, ethyl, propyl, isopropyl, halogen, methyl ether, methyl ketone, and methyl ester;

$R_5$ and $R_6$ are each an $(CH_2)n_1$, where $n_1$ is 0-3, linked to a member selected from the group consisting of 1-3 adjacent amidines, 1-3 adjacent amines, 1-3 adjacent guanidines, benzamidine, 1-3 adjacent guanidines linked to a phenyl ring, amide, urea, carbamide, carbonate, carboxylate, anhydride, thioamide, thiourea, carboxylate, thiocarbamide, thiocarbonate, thioanhydride, hydroxyl, an ester (e.g., an alkyl ester, acyl ester, aryl ester, alkyl thioester, acyl thioester, aryl thioester), and $CZ_{1n}H_{3-n}$ where $Z_1$ is selected from the group consisting of halogen, methyl, ethyl, propyl, isopropyl, t-butyl, and sec-butyl, and n is 1 to 3;

$X_2$ is selected from the group consisting of sulfur, $SO_2$, SO, $NHSO_2$ methylene, oxygen, carbonyl, ethylene, amide, imine, ester and thioester;

$R_7$ and $R_8$ are each selected from the group consisting of halogen, methyl, ethyl, propyl, isopropyl, t-butyl, and sec-butyl and $CZ_{1n}H_{3-n}$ where $Z_1$ is halogen, and n is 1 to 3, e.g., 4-(4-{[(1,5-dimethyl-3-oxo-2-phenyl-2,3,dihydro-1H-pyrazol-4-yl)amino]sulfonyl}anilino)-4-oxo butanoic acid (Compound 4):

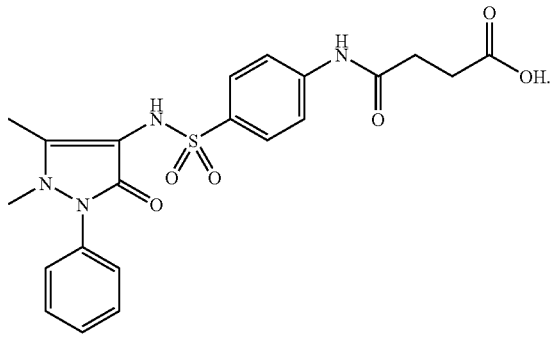

Formula (VII):

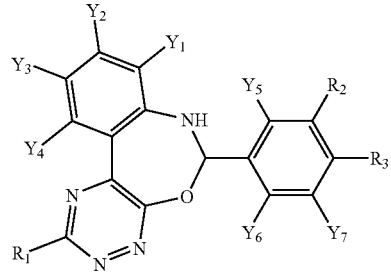

wherein $Y_1, Y_2, Y_3, Y_4, Y_5, Y_6,$ and $Y_7$ are each independently selected from the group consisting of hydrogen, methyl, ethyl, propyl, isopropyl, halogen, methyl ether, methyl ketone, and methyl ester;

$R_1, R_2$ and $R_3$ which may be the same or different are selected from the group consisting of 1-3 adjacent amidines, 1-3 adjacent amines, 1-3 adjacent guanidines, amide, urea, carbamide, carbonate, carboxylate, anhydride, thioamide, thiourea, carboxylate, thiocarbamide, thiocarbonate, thioanhydride, hydroxyl, an ester (e.g., an alkyl ester, acyl ester, aryl ester, alkyl thioester, acyl thioester, or aryl thioester), and CZnH3-n where Z is a halogen, and n is 1 to 3, e.g., 1,2-(3-methylthiotraizine),3,4-phenyl,6-[(2-methoxyphenoxy)Acetic Acid]morpholine (Compound 33):

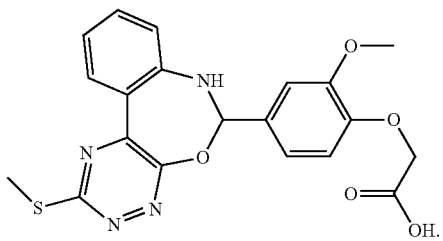

Formula (VIII):

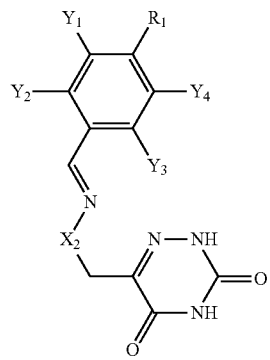

wherein $Y_1$, $Y_2$, $Y_3$ and $Y_4$ are each independently selected from the group consisting of hydrogen, methyl, ethyl, propyl, isopropyl, halogen, methyl ether, methyl ketone, and methyl ester;

$R_1$ is selected from the group consisting of 1-3 adjacent amidines, 1-3 adjacent amines, 1-3 adjacent guanidines, amide, urea, carbamide, carbonate, carboxylate, anhydride, thioamide, thiourea, thiocarbamide, thiocarbonate, thioanhydride, hydroxyl, an ester (e.g., an alkyl ester, acyl ester, aryl ester, alkyl thioester, acyl thioester, or aryl thioester), and $CZ_nH_{3-n}$ where Z is a halogen, and n is 1 to 3;

$X_2$ is selected from the group consisting of sulfur, $SO_2$, SO, NHSO2 methylene, oxygen, carbonyl, ethylene, amide, imine, ester and thioester, e.g., 4-{[2-(3,5-Dioxo-2,3,4,5-tetrahydro-[1,2,4]triazin-6-yl)-acetyl]-hydrazonomethyl}-benzoic acid (Compound 51):

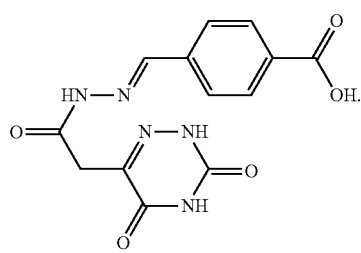

Formula (IX):

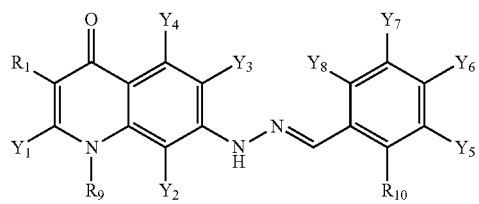

wherein $Y_1$, $Y_2$, $Y_3$, $Y_4$, $Y_5$, $Y_6$, $Y_7$, and $Y_8$ are each independently selected from the group consisting of hydrogen, methyl, ethyl, propyl, isopropyl, halogen, methyl ether, methyl ketone, and methyl ester;

$R_1$ is selected from the group consisting of 1-3 adjacent amidines, 1-3 adjacent amines, 1-3 adjacent guanidines, amide, urea, carbamide, carbonate, carboxylate, anhydride, thioamide, thiourea, thiocarbamide, thiocarbonate, thioanhydride, hydroxyl, an ester (e.g., an alkyl ester, acyl ester, aryl ester, alkyl thioester, acyl thioester, or aryl thioester), and $CZ_nH_{3-n}$ where Z is a halogen, and n is 1 to 3;

$R_9$ is selected from the group consisting of methyl, ethyl, isopropyl, butyl, t-butyl, and sec-butyl;

$R_{10}$ is a negatively charged functional group (e.g., $NO_2$ or $SO_2$), e.g., 1-Ethyl-6-fluoro-7-[N'-(2-nitro-benzylidene)-hydrazino]-4-oxo-1,4-dihydro-quinoline-3-carboxylic acid (Compound 24):

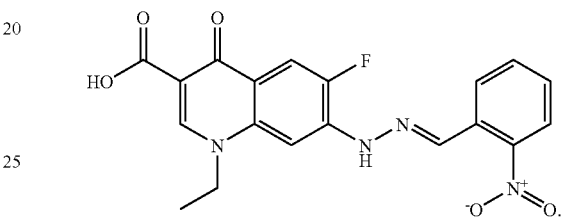

Formula (X):

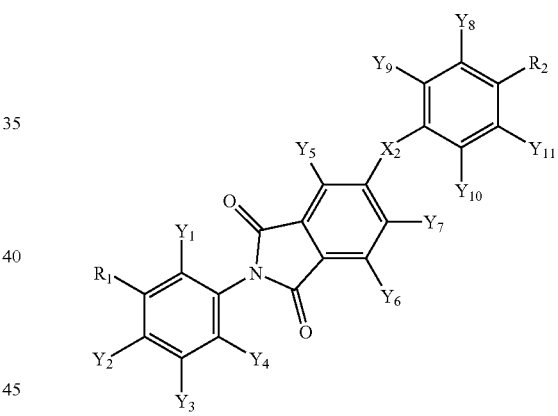

wherein $Y_1$, $Y_2$, $Y_3$, $Y_4$, $Y_5$, $Y_6$, $Y_7$, $Y_8$, $Y_9$, $Y_{10}$, and $Y_{11}$ are each independently selected from the group consisting of hydrogen, methyl, ethyl, propyl, isopropyl, halogen, methyl ether, methyl ketone, and methyl ester;

$R_1$ and $R_2$ which may be the same or different are selected from the group consisting of 1-3 adjacent amidines, 1-3 adjacent amines, 1-3 adjacent guanidines, amide, urea, carbamide, carbonate, carboxylate, anhydride, thioamide, thiourea, thiocarbamide, thiocarbonate, thioanhydride, hydroxyl, an ester (e.g., an alkyl ester, acyl ester, aryl ester, alkyl thioester, acyl thioester, or aryl thioester), and $CZ_nH_{3-n}$ where Z is a halogen, and n is 1 to 3;

$X_2$ is selected from the group consisting of sulfur, $SO_2$, SO, methylene, oxygen, carbonyl, ethylene, amide, imine, ester and thioester, e.g., (3-benzoic)-1,3,dioxo-2,3-dihydro-1H-isoindole-5-sulfanyl-4-benzoic acid (Compound 38):

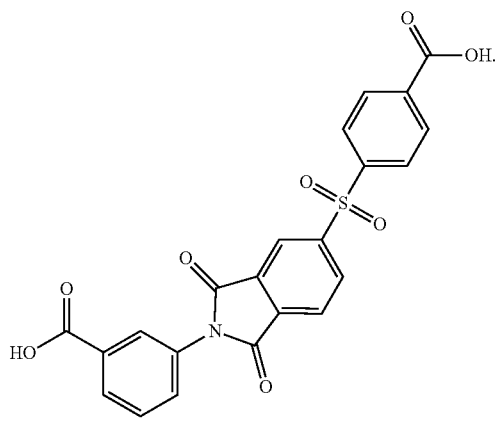

Formula (XI):

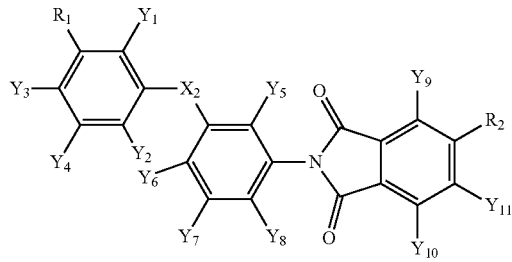

wherein $Y_1$, $Y_2$, $Y_3$, $Y_4$, $Y_5$, $Y_6$, $Y_7$, $Y_8$, $Y_9$, $Y_{10}$, and $Y_{11}$ are each independently selected from the group consisting of hydrogen, methyl, ethyl, propyl, isopropyl, halogen, methyl ether, methyl ketone, and methyl ester, $R_1$ and $R_2$ which may be the same or different are selected from the group consisting of 1-3 adjacent amidines, an amine, 1-3 adjacent amines, guanidine, 1-3 adjacent guanidines, amide, urea, carbamide, carbonate, carboxylate, anhydride, thioamide, thiourea, thiocarbamide, thiocarbonate, thioanhydride, hydroxyl, an ester (e.g., an alkyl ester, acyl ester, aryl ester, alkyl thioester, acyl thioester, or aryl thioester), and CZnH3-n where Z is a halogen, and n is 1 to 3;

$X_2$ is selected from the group consisting of sulfur, $SO_2$, SO, $NHSO_2$ methylene, oxygen, carbonyl, ethylene, amide, imine, ester and thioester, e.g., 2-[3-(3-Hydroxy-phenylcarbamoyl)-phenyl]-1,3-dioxo-2,3-dihydro-1H-isoindole-5-carboxylic acid (Compound 39):

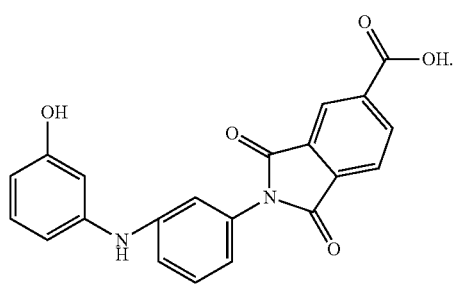

Formula (XII):

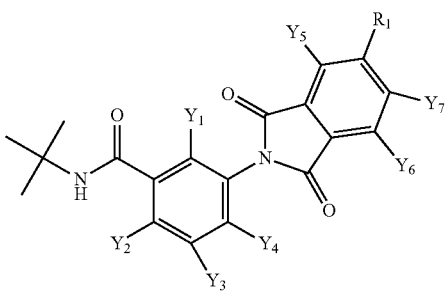

wherein $Y_1$, $Y_2$, $Y_3$, $Y_4$, $Y_5$, $Y_6$, and $Y_7$ are each independently selected from the group consisting of hydrogen, methyl, ethyl, propyl, isopropyl, halogen, methyl ether, methyl ketone, and methyl ester;

$R_1$ is selected from the group consisting of 1-3 adjacent amidines, 1-3 adjacent amines, 1-3 adjacent guanidines, amide, urea, carbamide, carbonate, carboxylate, anhydride, thioamide, thiourea, thiocarbamide, thiocarbonate, thioanhydride, hydroxyl, an ester (e.g., an alkyl ester, acyl ester, aryl ester, alkyl thioester, acyl thioester, or aryl thioester), and $CZ_nH_{3-n}$ where Z is a halogen, and n is 1 to 3, e.g., 2-(3-tert-Butylcarbamoyl-phenyl)-1,3-dioxo-2,3-dihydro-1H-isoindole-5-carboxylic acid (Compound 44):

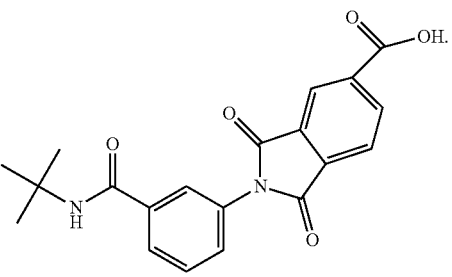

Formula (XIII):

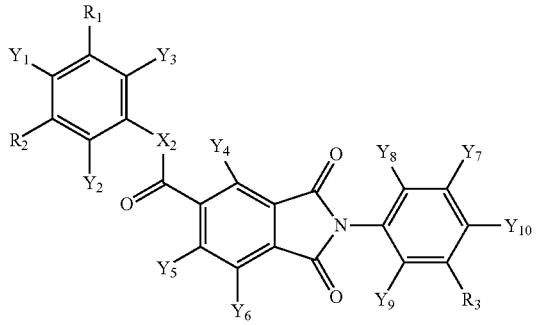

wherein $Y_1$, $Y_2$, $Y_3$, $Y_4$, $Y_5$, $Y_6$, $Y_7$, $Y_8$, $Y_9$, and $Y_{10}$ are each independently selected from the group consisting of hydrogen, methyl, ethyl, propyl, isopropyl, halogen, methyl ether, methyl ketone, and methyl ester;

$R_1$, $R_2$ and $R_3$ which may be the same or different are selected from the group consisting of 1-3 adjacent amidines, 1-3 adjacent amines, 1-3 adjacent guanidines, amide, urea, carbamide, carbonate, carboxylate, anhydride, thioamide, thiourea, thiocarbamide, thiocarbonate, thioanhydride, hydroxyl, an ester (e.g., an alkyl ester, acyl ester, aryl ester, alkyl thioester, acyl thioester, or aryl thioester), and $CZ_nH_{3-n}$ where Z is a halogen, and n is 1 to 3;

$X_2$ is selected from the group consisting of sulfur, $SO_2$, SO, $NHSO_2$, methylene, oxygen, carbonyl, ethylene, amide, imine, ester and thioester, e.g., 5-{[2-(3-Methoxy-phenyl)-1,3-dioxo-2,3-dihydro-1H-isoindole-5-carbonyl]-amino}-isophthalic acid (Compound 45):

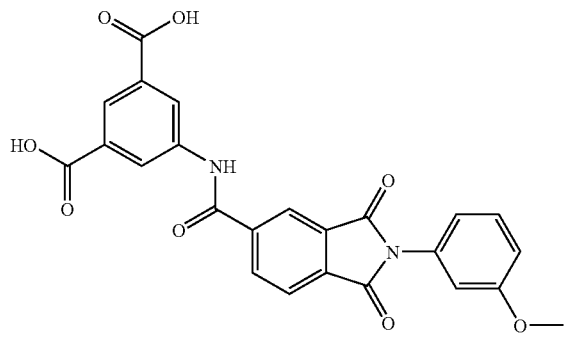

Pentamidine (Sigma Chemicals; catalogue #P0547), Compound 1 (Maybridge Chemical Company, Ltd.; catalogue # SPB03102), Compound 3 (Maybridge Chemical Company, Ltd.; catalogue #RJF01370), Compound 4 (Maybridge Chemical Company, Ltd.; catalogue #BTB12151), Compound 9 (Maybridge Chemical Company, Ltd.; catalogue # RFJ00706), Compound 24 (Chembridge Corporation; catalogue #5954029), Compound 31 (Chembridge Corporation; catalogue #5658092), Compound 33 (Chembridge Corporation; catalogue #5720358), Compound 38 (Chembridge Corporation; catalogue #5740132), Compound 39 (Chembridge Corporation; catalogue #5748750), Compound 44 (Chembridge Corporation; catalogue #5774211), Compound 45 (Chembridge Corporation; catalogue #5764589) and Compound 51 (Chembridge Corporation; catalogue #6050433) are available from commercial sources.

The compounds of formulae (I)-(XIII) can be prepared conventionally, using known reaction chemistry, starting from known materials or materials conventionally preparable (see Houben-Weyl, Methoden der Organischen Chemie, *Methods of Organic Chemistry*, Georg-Thieme-Verlag, Stuttgart), and/or can be generated from commercially available compounds by routine chemical modifications.

For example, derivatives of pentamidine of formula (I) can be prepared as described by Nandi et al, *J. Ind. Chem. Soc.*, 70:527 (1993), as shown in FIG. 15. 4-cyanophenol is alkylated with a series of polymethylene dibromides to give the corresponding bis(4-cyanophenyloxy)alkanes (1a-1e). This is followed by conversion of the cyano intermediates to a series of imidate hydrochlorides, which are converted to their corresponding free bases (2a-2e) by treatment with aqueous sodium hydroxide. Imidates 2a-2e are then treated with the ammonium salt of isethionic acid to give the final target Compounds 3a-3e (see FIG. 15). By varying the starting compounds in this synthetic route and/or reactants at various stages in this reaction scheme, various substituents ($Y_1$-$Y_8$; $R_1$-$R_2$; and varying lengths of X, n=1-8) can routinely be substituted to make derivatives of pentamidine as represented in formula (I).

In a second example (i.e., for Compound 4), the routine synthesis of Compound 4 is outlined below:

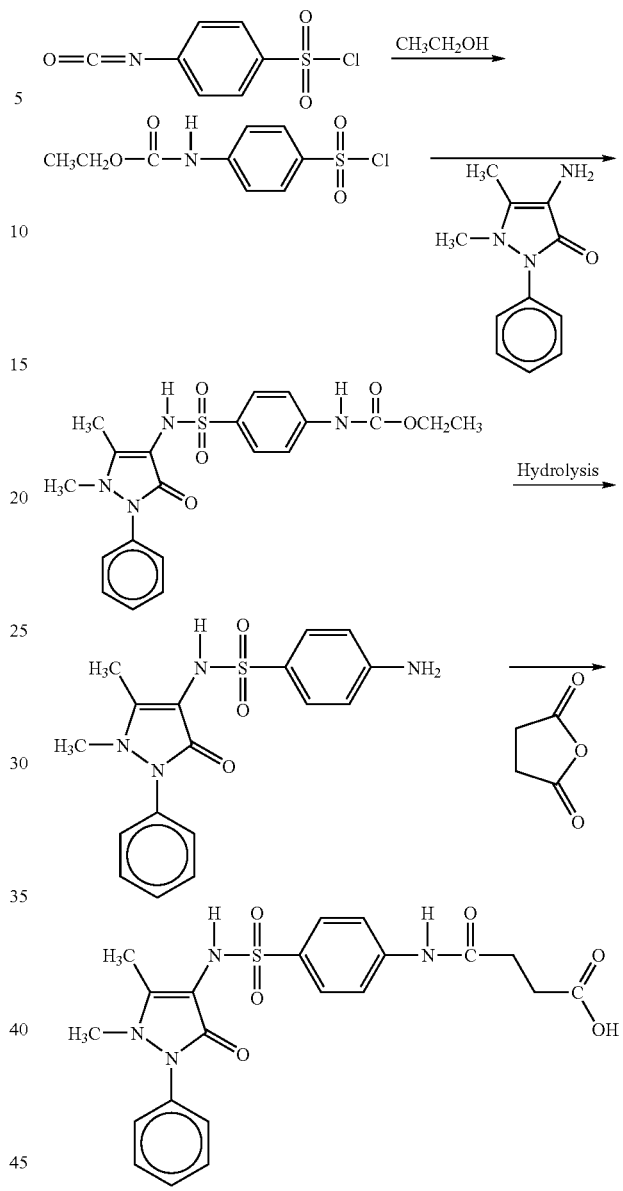

Compound 4

By varying the starting compounds in this synthetic route (i.e., for Compound 4) and/or reactants at various stages in this reaction scheme, various substituents ($Y_1$-$Y_9$; $R_5$-$R_8$; and the $X_2$ linker) can routinely be substituted to make derivatives of Compound 4 as represented by formula (VI). Using an approach similar to that described by these two examples (formulae (I) and (VI)), routine modifications to other known synthetic pathways (i.e., for the preparation of Compounds 1, 3, 9, 24, 31, 33, 38, 39, 44, 45 and 51) can be made to prepare the compounds represented in formulae (II), (III), (IV), (V), (VII), (VIII), (IX), (X), (XI), (XII) and (XIII).

The particular pharmaceutically acceptable salt is not critical to the present invention and may include isethionate, HCl, oxalacetate, or other salts.

The compounds of the present invention can be present in a composition, e.g., a pharmaceutical composition useful for treating cancer, along with a pharmaceutically acceptable carrier or diluent.

The particular pharmaceutically acceptable carrier or diluent employed in the present invention is not critical thereto. Examples of such carriers or diluents are listed in The Handbook of Pharmaceutical Excipients, A. Wade and P. J. Weller, Eds., 2$^{nd}$ Edition, American Pharmaceutical Association, Washington D.C. (1994) (which is incorporated herein by reference). Cremophore EL is preferred.

The particular mode of administration of the compounds represented by formulae (I)-(XIII) of the present invention is not critical thereto. For example, the compounds may be administered topically to skin cancers as in an ointment or cream. Intravenous administration using phosphate buffer-saline solution is another option.

The particular amount of the compound represented by formula (I) to (XIII) to be administered in accordance with the present invention varies depending upon the mode of administration, the cancer to be treated, whether administered alone or in combination with other drugs, and the age, weight and sex of the subject to be treated. Generally, the amount to be administered topically is in the range of about 1 to 300 mg/m$^2$ of body surface, preferably 20-300 mg/m$^2$ of body surface.

The cancers on which the compounds of the present invention exhibit a pharmaceutical effect are not particularly limited. However, the compounds of the present invention are particularly effective against melanomas, astrocytomas, gliomas as well as other cancers with elevated S100B or other S100 proteins, such as cancers of the brain, lung, bladder, intestine, kidney, cervix, breast, skin, head and neck, lymph, testes, larynx and mouth.

Inhibition of binding of S100 proteins to p53 can be assayed by fluorescence binding/competition assays. For example, binding to S100B is monitored using fluorescent peptides such as the F43W p53 peptide (SHLKSKKGQSTSRHKKLMWKTE (SEQ ID NO:1)) or the TRTK-12 peptide (TRTKIDWNKIL (SEQ ID NO:2)) that both contain fluorescent tryptophan residues (see Example 7). In such an assay, the binding of the peptide is monitored by changes in its fluorescence intensity at 350-370 nm in the presence of 10-20 mM calcium chloride (pH 7.4). Displacement of the peptide by the test compound is then monitored by a corresponding decrease in fluorescence intensity and the dissociation constant of the test compound from S100B is calculated using a standard competition equation ($K_D=K_{app}/$ (1+[floursecent peptide]/$K_D$ peptide). The amino acid residues on S100B to which the test compound binds can then be monitored by chemical shift perturbations using NMR spectroscopy.

Overexpression of S100 proteins, such as S100B, due to p53 activation can be measured by Western blotting techniques (see FIG. 11 and Example 1).

The following examples are provided for illustrative purposes only and are in no way intended to limit the scope of the invention.

Example 1

Wild-Type S100B and p53 Protein Levels in Primary Malignant Melanoma Cells

Western blot analyses were performed, as described previously (Lin et al, supra), on 100 μg of primary human melanoma C8146A protein extracts or on 100 μg of human glioblastoma U118 protein extracts.

The C8146A cells were obtained from Dr. Frank L. Meyskens (University of California, Irvine), and grown in F-10 media containing 10% (v/v) Fetal Calf Serum (FCS, GIBCO-BRL).

The U118 cells were purchased from American Type Culture Collection (ATCC, Manassas, Va.), and grown in D-MEM containing 10% (v/v) FCS.

The cells were lysed in RIPA buffer comprising 50 mM Tris-HCl (pH 7.5), 150 mM NaCl, 1.0% (v/v) Nonidet P-40, 0.5% (w/v) sodium deoxycholate, 0.1% (w/v) SDS, 1.0 mM PMSF, 10 μg/ml aprotinin, 2.0 μg/ml leupeptin and 5.0 mM DTT to obtain the cell extracts.

The proteins in the cell extracts were run on a 12% (w/v) polyacrylamide gel, transferred to nitrocellulose and reacted with either p53 mouse monoclonal antibody (DO-1, Oncogene Research Products, Boston, Mass.) at 1:1000 dilution, S100B rabbit polyclonal antibody (Research Diagnostics Inc., Flanders, N.J.) at a 1:500 dilution, cyclin D1 monoclonal antibody (Oncogene Research Products) at a 1:100 dilution, or actin mouse monoclonal antibody (Oncogene Research Products) at a 1:5000 dilution to control for even protein loading. The blots were then reacted with their respective secondary antibodies conjugated to horseradish peroxidase and reacted with a chemiluminescence substrate (ECL, Amersham Pharmacia Biotech Inc, Piscataway, N.J.) as recommended by the manufacturer. Recombinant S100B protein control was produced and purified to homogeneity as described previously (Lin et al, supra). The results are shown in FIGS. 2A-2B.

Figure 2A:
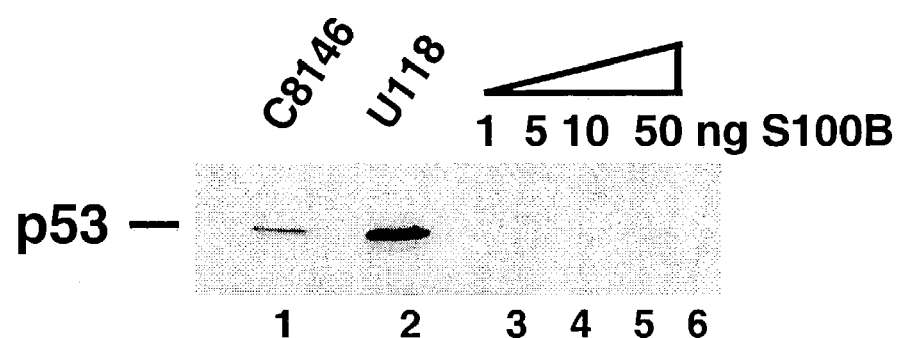
Figure 2B:
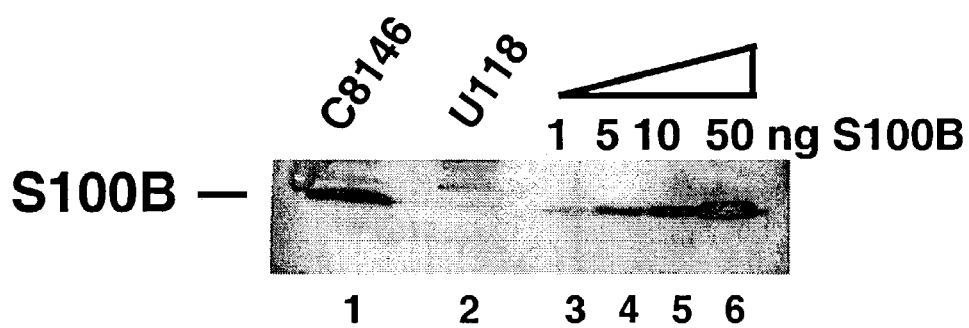

As shown in FIGS. 2A-2B, primary malignant melanoma cells (C8146) established relatively high levels of S100B, but p53 levels were markedly lower in these cancer cells as compared to cells with little or no S100B (i.e., U118). This observation in vivo is consistent with what is found in transient co-transfections of S100B and p53, where levels of the tumor suppressor protein were significantly reduced by the addition of S100B (>100-fold) (Lin et al, supra). Using increasing amounts of S100B recombinant protein, it was estimated that the levels of S100B in C8146 cells are at least fifty times higher than in U118 cells.

Example 2

Figure 3:
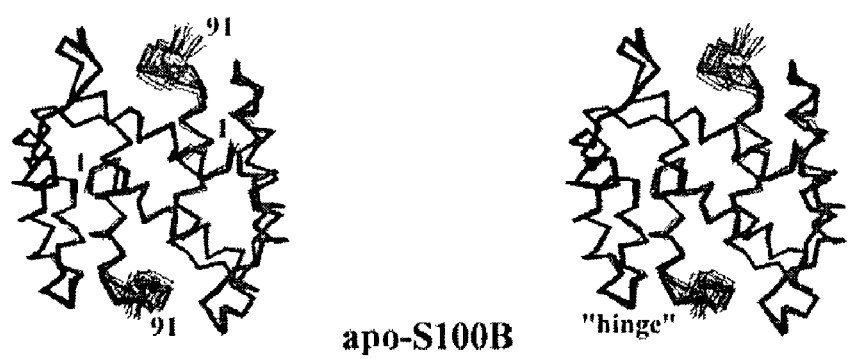
FIG. 3 shows a stereo view of 20 NMR structures of dimeric apo-S100B (ββ) with the two S100β subunits shown in blue and red.

The S100B and p53 Interaction is Calcium-Dependent (A) Solution Structure of apo-S100B and Ca$^{2+}$-Bound S100B The 3-D solution structure of dimeric apo-S100B was determined using distance, dipolar coupling, and dihedral angle constraints. The α-helical content of apo-S100B (Amburgey et al, *J. Biomol. NMR*, 6:171-179 (1995)) and ambiguity arising from its symmetric dimer interface complicated the NOE assignments. Therefore, 2D and 3D NOESY spectra were supplemented with 4D NOESY experiments to resolve overlap problems and $^{13}$C-edited, $^{12}$C-filtered experiments with asymmetrically labeled S100B (i.e., 1:1 mixture of unlabeled: $^{13}$C,$^{15}$N-labeled S100B) were used to distinguish intra- from intermolecular NOE correlations at the dimer interface (Drohat et al, supra). As a result, over 70% of the long-range and intermolecular NOE correlations were assigned based on chemical shift values alone. Because NOE-based structures are based only on short-range distance constraints, the structure was refined using long-range dipolar coupling constraints (Tjandra et al, *Science*, 278:1111-1114 (1997); Tjandra et al, *Nat. Struct. Biol.*, 4:443-449 (1997); and Drohat et al, *Biochemistry*, 37:2729-2740 (1998)). The solution structure of apo-S100B was published at very high resolution (Q≈0.3) (Drohat et al (1996), supra; and Drohat et al, *Protein Science*, 8:800-809 (1999)), and is shown in FIG. 3. In fact, in regions where there is little dynamic character, the quality factor is even better (Q<0.2). The final structure (~15 distance NMR constraints/residue) of apo-S100B illustrates the symmetric dimer interface with the perpendicular association of pairs of antiparallel helices that forms an X-type four-helical bundle (FIG. 3). As a result of this fold, the C-terminal EF-hand of apo-S100B is different from that of calmodulin, troponin C, calbindin $D_{9k}$, calcyclin, and parvalbumin (Drohat et al (1996), supra; and (Drohat et al (1999), supra); it also has an extensive hydrophobic core and a charged surface consistent with its high solubility. As for the apo-protein, the solution structure of $Ca^{2+}$-bound S100B (FIG. 1) was solved using NMR and is shown in Drohat et al (1998), supra and FIG. 4.

(B) The S100B Dimer and the Conformational Change

Figure 1:
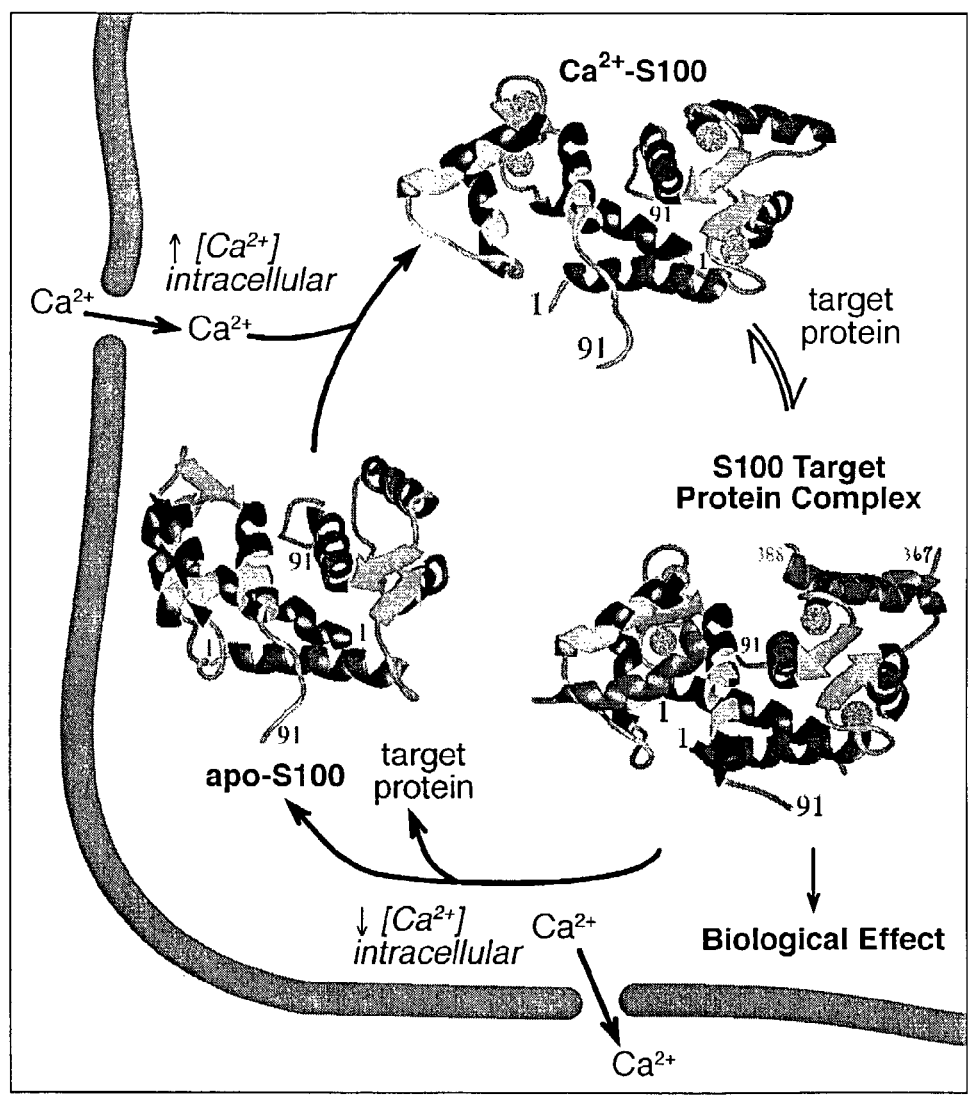
Figure 4:
FIG. 4 shows a stereo view of the backbone superposition of the 40 calculated NMR structures of the negative regulatory domain of p53 complexed to the $Ca^{2+}$-loaded S100B dimer. Helices of the two different S100β subunits are colored in blue and red, $Ca^{2+}$ ions are light purple, and the C-terminus (residues 367-388) from two subunits of p53 are colored green.

Comparison of the apo- (FIG. 3) and $Ca^{2+}$-bound (FIG. 4) structures of S100B showed no differences in the orientation of helices (1, 1', 4, or 4') in the X-type four helical bundle dimer interface (FIG. 1). These findings confirm the gel filtration, light scattering, and analytical ultracentrifugation data described in Drohat et al, *Protein Science*, 6:800-809 (1997); Landar et al, *Biochim Biophys Acta*, 1343:117-129 (1997); and Landar et al, *Biochem.*, 37:17429-17438 (1998), which indicates that the S100B dimer is stable below 1.0 nM concentrations both in the presence and absence of $Ca^{2+}$ (Drohat et al (1997), supra; Landar et al (1997), supra; and Landar et al (1998), supra). Thus, the noncovalent dimer is the state of S100 proteins inside cells and the NMR structures are of the physiologically relevant oligomerization state. In the second EF-hand (the typical EF-hand), however, there is a large change in the position of helix 3 upon the addition of $Ca^{2+}$ (FIG. 1). In this EF-hand, a 90° change is observed in the interhelical angles between helices 3 and 4 upon the addition of $Ca^{2+}$. This $Ca^{2+}$-dependent conformational change exposes a cleft defined by residues in the hinge region, the C-terminal loop, and helix 3, which is absent in the apo-structure (FIG. 1). The exposure of this surface on $Ca^{2+}$-bound S100B, colored yellow in FIG. 1, is necessary for p53 binding (FIG. 1 and FIG. 4).

(C) Solution Structure of the $Ca^{2+}$-S100B-p53 Peptide Complex

To explore the details of the interaction between S100B and the C-terminus of p53, titrations of $Ca^{2+}$-bound S100B with the $p53^{367-388}$ peptide were monitored by NMR spectroscopy as described in Rustandi et al (2000), supra; Rustandi et al (1998); supra; and Rustandi et al, *Protein Science*, 8:1743-1751 (1999). In the presence of $Ca^{2+}$, a large number of resonances from S100B in the HSQC spectrum shifted significantly upon the addition of $p53^{367-388}$, but no changes were observed in the absence of $Ca^{2+}$. These data confirmed the $Ca^{2+}$-dependence of the p53 peptide interaction with S100B. The size (26 kDa) and complexity of the S100B-p53 quaternary complex (two p53 peptides per S100B dimer) required the collection of heteronuclear multidimensional (2D-4D) NMR data (Clore et al, *Determination of structures of larger proteins in solution by three- and four-dimensional heteronuclear magnetic resonance spectroscopy*. NMR of proteins (Clore et al, Eds.), CRC Press, Boca Raton, Fla. (1993); and Walters et al, *Methods Enzymol.*, 339:238-258 (2001)) with samples that were labeled both symmetrically (both subunits of S100B are fully isotopically labeled; p53 is unlabeled) and asymmetrically (50:50 mixture of labeled and unlabeled S100β subunits; p53 is unlabeled). These NMR data and the structure of the S100B-p53 peptide complex are described in Rustandi et al (2000) (supra). In total, 3,466 experimental constraints (~15/residue) were used to calculate the structure of $p53^{367}$-388 bound to $Ca^{2+}$-S100B (FIG. 4).

(D) The $Ca^{2+}$-Dependence of the p53-S100B Interaction

The $Ca^{2+}$-dependence of the S100B-p53 interaction can be observed by comparing the structures of all three S100B complexes (apo-, $Ca^{2+}$-bound, and p53-bound S100B; FIG. 1). Most of the residues that interact with p53 (18 of 21) are buried in the apo-S100B structure (colored yellow in FIG. 1). When $Ca^{2+}$ binds to S100B, however, these same residues are exposed due to a large change in the position of helix 3; this conformational change is required for the interaction with the p53 (FIG. 1). This structure was also useful for understanding the consensus sequence (i.e., from phage peptide library screen) found in S100B protein targets. Much of the 'S100B-consensus sequence' is found in the C-terminus of p53 (Ivanenkov et al, *J. Biol. Chem.*, 270:14651-14658 (1995)), and when the p53 peptide is mutated (F385W) to better match this sequence, the affinity of the p53 peptide for S100B goes up 5-fold (Rustandi et al (1998), supra). The 3D structure/dynamic studies of S100B bound to a 12-residue peptide comprising the entire consensus sequence (TRTK-12 peptide) is described in Inman et al, *J. Mol. Biol.*, 324:1003-1014 (2002), so both the TRTK-S100B and p53 S100B structures were used herein in drug design efforts.

Example 3

The Interaction Between S100B and p53 in Malignant Melanomas is Cell Cycle-Dependent To study whether the interaction between S100B and p53 in malignant melanomas is cell cycle-dependent, C8146A primary malignant melanoma were synchronized by serum starvation (0.5% (w/v)). Specifically, synchronization of the melanoma cells was performed by serum starvation by growing the cells in 0.5% (v/v) FCS for 48 hrs and then increasing the FCS levels to 15% (v/v), and then growing the cells for varying time periods (i.e., between 0 and 48 hrs) prior to harvesting. The cells were then harvested and washed twice with ice-cold PBS. Next, the cell pellets were lysed in lysis buffer comprising 50 mM Tris-HCl (pH 7.5), 150 mM NaCl, 2.0 mM $CaCl_2$, 1.0 mM PMSF, 2.0 µg/ml leupeptin and 5.0 mM DTT. The cells, containing ½ volume 0.1 mm glass-beads, were frozen and thawed three times and centrifuged at 15,000 rpm. The supernatant (1.0 mg) was incubated with either p53 antibody (DO-1) or S100B antibody for 2 hrs at 4° C. Protein A-Agarose beads (50 µl, Oncogene) were then added and the samples were incubated overnight at 4° C. The beads were spun down and washed six times with lysis buffer, and loaded on a 12% (w/v) SDS-PAGE. The samples were transferred to a nitrocellulose membrane and incubated, i.e., co-immunoprecipitated with S100B antibody or p53 antibody as described above. The results are shown in FIGS. 5A-5B.

As shown in FIGS. 5A-5B, a direct S100B-p53 interaction occurs in vivo. S100B is predominantly cytosolic in most cells, while p53 is localized in the cytoplasm during $G_1$ and enters the nucleus during S to initiate transcription activation. The data shown in FIG. 5A indicate that expression of cyclin D1, a $G_1$ marker, was maximal between 6 to 8 hrs following the release of the melanoma cells in 15% (v/v) serum. For this reason, the 6 hr time point was chosen to prepare the synchronized $G_1$ extracts for the cancer cells. Immunoprecipitation of asynchronous exponentially growing cancer cells with p53 antibody (FIG. 5B, lane 1) indicate that only a small amount of S100B, if any, can be co-immunoprecipitated with p53. However, when the cells were synchronized in $G_1$ (FIG. 5B, lane 3), the amount of S100B that can be immunoprecipitated with p53 antibody increased markedly. The reciprocal immunoprecipitation experiment performed with S100B antibody (FIG. 5B, lane 2) confirmed the formation of a complex between p53 and S100B during $G_1$. The fact that this interaction occurs in $G_1$ is significant because this phase precedes DNA replication, and is an important checkpoint for p53 response to damaged DNA. In most cells, p53 is localized in the cytoplasm during $G_1$ and enters the nucleus during S to provide its transcriptional activity. One important downstream effector gene of p53 is the cyclin dependent kinase inhibitor p21. This inhibitor prevents phosphorylation of pRb and arrests the cells in $G_1$ in response to DNA damage. It is thought that this arrest in $G_1$ allows cells time to repair their DNA and prevents the transmission of damaged DNA to daughter cells. Interaction of S100B with p53 in the cytosol during $G_1$ could prevent the entry of p53 to the nucleus during S and inhibit p53 transcriptional activity. The overall effect of S100B on wild-type p53 could mimic cellular aberrations such as gene amplification and mutations that are encountered with non-functional p53. While most proteins that bind or modify the C-terminus of p53 activate the tumor suppressor, the opposite effect was observed for S100B. p53 function was decreased when bound to S100B (Lin et al, supra).

Example 4

S100B Inhibition of p53 Function

S100B inhibits phosphorylation of p53 (Wilder et al, supra; and Rustandi et al (1998), supra), and disrupts p53 tetramers (Baudier et al, supra), two functions important for p53 transcriptional activity (Giaccia et al, *Genes and Develop.,* 12:2973-2983 (1998)). S100B reduces p53 DNA-binding activity (Lin et al, supra), which suggests that in addition to inhibiting phosphorylation and preventing tetramer formation, S100B could also affect p53 transcriptional activity (Lin et al, supra). To verify this, transient transfections were carried out with S100B and p53 expression vectors concomitantly with a p53 reporter gene construct (pG13-CAT) (Kern et al, *Science,* 256:827-830 (1992)) in H1299 human large-cell lung carcinoma cells. Transfection of S100B alone did not affect the reporter gene, but co-transfection of S100B with p53 significantly reduced the transcriptional activity (Lin et al, supra). These studies with S100A1, and as for S100B, S100A1 inhibited p53 function (Carrier et al, supra). Studies done with mts1 show this S100 protein also binds p53 and significantly inhibits its transcription activation (Grigorian et al, supra).

To further assess the significance of the S100B interaction with p53, the protein levels of p53 and two of its downstream effector genes, mdm2 (or hdm2 for humans) and p21 were examined. Specifically, human large-cell lung carcinoma cells (H1299) were transiently co-transfected with p53 and S100B expression vectors. The H1299 cell line was obtained from Dr. Bert Vogelstein. These cells have a null p53 genotype due to homozygous deletion of the p53 gene, so the only p53 present was wild-type protein introduced via the transfection (Funk, *Mol. Cell Biol.,* 12:2866-2871 (1992)). The results are shown in FIG. 6A.

As shown, in FIG. 6A, p53 was not detected in the absence of p53 expression vector (lanes 1, 2; FIG. 6A); consequently, endogenous levels of mdm2 and p21 proteins were low. As expected, expression of p53 triggered expression of mdm2 and p21 (FIG. 6A, lane 3), but co-expression with the S100B protein reduced markedly the accumulation of p53 (>100-fold), mdm2 and p21 protein levels (FIG. 6A, lane 4). Expression of S100B (FIG. 6A, lane 2) in the absence of p53 (i.e., control experiment) did not affect significantly the basal levels of mdm2 or p21 (FIG. 6A). This data shows that reduction of p53, mdm2 and p21 levels is dependent on S100B.

Next, it was explored whether S100B could interact with endogenous p53 and affect the expression of mdm2 and p21. The human breast cancer cell line MCF-7, which has a wild type p53 genotype (Kastan et al, *Cell,* 71:587-597 (1992)), was transiently transfected with S100B. After S100B transfection, the cells were either treated (or not) with the x-ray mimic agent bleomycin to induce endogenous p53 production. The results are shown in FIG. 6B.

As shown in FIG. 6B, the basal levels of p53, mdm2 and p21 can be induced by exposure to bleomycin (FIG. 6B, lane 2). Endogenous S100B is undetectable in MCF-7 cells (FIG. 6B, lane 1), while over-expression of S100B protein reduces p53 levels, and blocked mdm2 and p21 accumulation (FIG. 6B, lane 4). These data show that S100B inhibits the endogenous expression of p53 downstream effector genes in vivo.

Example 5

Regions of the S100B Promoter Bind p53

When active p53 levels rise, the transcription of a number of genes involved in cell-cycle and apoptosis are activated. In one well-known case, p53 activates the transcription of mdm2, a protein that is involved in ubiquitin-dependent degradation of p53 itself as part of a feedback loop (Prives et al (1999), supra; Freedman et al, *Cell Mol. Life Sci.,* 55:96-107 (1999); and Momand et al, *Gene,* 242:15-29 (2000)). In an analogous situation to mdm2 (hdm2 in humans), the promoter for S100B has three sequences that correspond to the consensus sequence for p53 binding (FIG. 7). In fact, one sequence in the S100B promoter perfectly matches the p53-binding consensus sequence (20/20 nucleotide match; FIG. 7).

Accordingly, mobility shift assays were performed with purified p53 to determine if these sequences in the promoter of S100B were bona fide p53 binding sites, using the GADD45 sequence as a positive control. The electrophoretic mobility shift assays were performed, essentially as described by Carrier et al, *Mutation Res.,* 352:79-86 (1996), with the exception that salmon sperm DNA (1.0 µg) and purified recombinant p53 were used. The baculovirus expressed p53 was obtained from Protein Sciences Inc. (Baltimore, Md.). Baculovirus expressed p53 was used (0.6 and 3.0 µg) for binding to the GADD45 and the S100B oligonucleotides respectively. The probes were purified by reverse phase HPLC (Vydac C-4) and labeled with T4 polynucleotide kinase (New England BioLabs) as described previously (Carrier et al (1996), supra). Oligonucleotide sequences from the S100β promoter matching 20, 17 and 16 nucleotides of the 20 consensus p53 binding site were as follows:

sense 5'-GCC TGG GCA AGC TCT GTG CTT CAC AGA GCA AGC CTG TGT-3' (SEQ ID NO:3);

sense 5'-GTT CTG GGA CTT TCA CTA AAC TTC TCC TAC CAT-3'(SEQ ID NO:4); and sense 5'-CAG AGG GCA GGC CCG GCT GGG CCC TCC TGC TGA-3'(SEQ ID NO:5).

The results are shown in FIG. 8.

As shown in FIG. 8, a complex of lower mobility was generated with both GADD45 and the S100B (20/20 nucleotide) probes (lanes 2 and 5, respectively). Moreover, both bands were super-shifted by p53 antibody (lanes 3 and 6, respectively), and thus represent genuine p53 complexes. However, despite matching the consensus sequence perfectly, five times more protein and DNA were necessary to generate the protein-DNA complex with the S100B promoter sequence when compared to the GADD45 sequence. This may be due to the fact that two of the T/A variants in the consensus sequence are T in the GADD45 sequence, which is preferred, but are A in the S100B sequence (FIG. 7). Another difference between these p53 binding sites is the length of the intervening DNA sequence that links the two 10 nucleotide stretches of DNA that interact with p53 (11 nt vs. 0 nt; FIG. 7). Similar data were obtained with the two other p53 consensus sites in the S100B promoter; however, these sites had even lower affinity for p53 than the 20/20 sequence. Together, these data suggest that the induction of S100B transcription by p53 occurs only after genes with higher affinity p53 sites in their promoters are occupied. Furthermore, it is also likely that p53 regulates the transcription of other S100 proteins, such as S100A2 (Tan et al, *FEBS Letter*, 445:265-268 (1999)), by binding the p53-binding consensus sequences found in their promoter regions (FIG. 7).

Example 6

Inhibition of the S100B-p53 Interaction Restores p53 Tumor Suppressor Function

Primary malignant melanoma cells C8146 have relatively high levels of S100B, but p53 levels are markedly lower in these cancer cells as compared to cells with little or no S100B (i.e., U118; FIGS. 2A-2B). This observation in vivo is consistent with what is found in transient co-transfections of S100B and p53, where levels of the tumor suppressor protein were significantly reduced by the addition of S100B (>100-fold) (Lin et al, supra). Using increasing amounts of S100B recombinant protein, the levels of S100B in C8146 cells were estimated to be at least fifty times higher than in U118 cells. To determine whether S100B contributes directly to low p53 levels in the melanoma cancer cells, small interfering RNA (siRNA) corresponding to the C-terminus of S100B was prepared and introduced into the melanoma cells.

The small interfering RNA (siRNA) used consisted of 23 nucleotides (nt) double-stranded RNA, which was synthesized by Xeragon Inc. (Huntsville, Ala.). The sequence of the siRNA, i.e., 5'-ACU ACU GCC UGC CAC GAG UUC-3' (SEQ ID NO:6), corresponds to the S100β C-terminal end (nt 244-265) plus two dT 3' overhang.

Different concentrations of siRNA (2.0, 20 nM) were added to the cells along with 2.0 µg of pCMV.3 empty vector (Stratagene, La Jolla, Calif.). The siRNA was transfected in C8146A melanoma cells using FuGENE reagent (Roche Molecular Biochemicals, Indianapolis, Ind.) according to the manufacturer's recommendation. The cells were harvested 24 hrs later and analyzed by Western blots as described above. The results are shown in FIG. 9.

As shown in FIG. 9, the addition of the S100B antisense RNA lowered S100B levels (3-fold) and correspondingly, increases in p53 levels (2.3-fold) were observed. Likewise, levels of the p21 protein, a gene activated by p53, were also up-regulated by the addition of siS100B (2.6-fold) as expected when p53 levels go up (FIG. 9). Together, these results with anti-sense RNA indicate that S100B contributes to down-regulation of functional p53 inside primary malignant melanoma cancer cells.

Example 7

Small Molecular Inhibitors of S100B

The above studies motivated the designing of small molecular inhibitors of S100B in order to restore wild-type p53 activity in cells with elevated levels of S100 proteins and reduced p53 levels, such as those in many cancers (i.e., malignant melanoma).

The small molecules were designed to inhibit the S100B-p53 interaction by binding to the p53 binding site on S100B and prevent p53 binding. Thus, such inhibitors are believed to protect p53 from S100B-dependent degradation pathways and restore wild-type p53 function inside cells. It was found in the present invention that combining computer-aided drug design (CADD) (Martin, *J. Med. Chem.*, 35:2145-2154 (1992); Ewing et al, *J. Comput. Chem.*, 18:1175-1189 (1997); Makino et al, *J. Comput. Aided Mol. Des.*, 13:513-532 (1999); and Hicks et al, *Curr. Opin. Drug Disc. & Devel.*, 1:223-234 (1998)), and structure activity relationship studies by NMR (SAR by NMR) (Hajduk et al, *Science*, 278:497-499 (1997); and Fesik, *J. Biomolecular NMR*, 3:261-269 (1994) (FIG. 10) is an effective way to identify novel small molecules that bind S100B and then block the S100B-p53 interaction. CADD is attractive because the search focuses on available compounds, thereby avoiding chemical synthesis in the beginning stages. Molecules were computationally selected from a 3D database of 1 million compounds and "placed" in the p53 binding site of S100B (FIG. 10). The orientation and conformation of the small molecules were then adjusted to maximize the fit into the S100B structure. Those molecules with favorable interaction energy and a number of possible ligand-receptor hydrogen bonds were selected for testing. SAR by NMR techniques (Hajduk et al, supra; and Fesik, supra) and thermodynamic binding studies of promising compounds were used to evaluate the binding site and affinity for S100B.

Over 1 million compounds were screened using CADD from which more than 50 molecules that bind to S100B were identified ($K_D$=500 nM-10 µM; from fluorescence binding assays) using biophysical and biological screens. One such molecule, pentamidine, is particularly interesting because (i) it is FDA approved for another use; and was found herein (see below) (ii) to bind to S100B ($K_D$=700 nM) in the p53 binding site as determined by NMR and fluorescence spectroscopy; (iii) it enters primary human malignant melanoma cells (wild-type p53) and inhibits their growth by more than eight-fold with a much lesser effect on normal melanocytes (8-fold); (iv) that treatment therewith partially restored p53 protein levels suggesting that such disrupts the S100-p53 complex; (v) that the p53 released up-regulates mdm2 and p21 as detected by Western blots and (vi) the S100B protein levels were increased by more than 10-fold in the primary melanomas (FIG. 11). The up-regulation of S100B is not surprising because it was discovered herein that the S100B gene is under transcriptional regulation of p53; in the S100B promoter there is a nucleotide sequence (nt 1705-1735) with an exact match (20 out of 20) to the p53 DNA-binding consensus sequence. DNA band shift assays show that p53 binds this site, as well as two other p53 sites in the S100B promoter, being more specific for the perfect match sequence (FIG. 7). These data imply that the drug is disrupting the S100B-p53 interaction and that the restoration of p53 transcriptionally activates p53 target genes such as p21, mdm2, and S100B.

(a) Binding Titrations

The binding of the small molecules to S100B identified in the CADD search were measured using fluorescence spectroscopy. The compounds identified are as follows:

Pentamidine isethionate ($K_d$=1.4+/−1 µM $IC_{50}$~500 nM); {[(2,3,dichloroanilino)(imino)methyl]amino}methanimidamide ($K_d$<1 µM $IC_{50}$<2.5) (Compound 3); {[(2-benzoyl-4-chloro anilino)(imino)methyl]amino}methanimidamide ($K_d$=4+/−1 µM) (Compound 9);

2-[2-(3-nitrophenyl)-2-oxoethoxy]-5-(tri-fluoromethyl)pyridinium-1-olate ($K_d$=2.7+/−1 µM $IC_{50}$=2.5 µM) (Compound 1); 2-Chloro-5-[N'(5-(3-chloro-4-benzoic)-furan-2ylmethylene-hydrazino]-benzoic acid ($K_d$~6 µM $IC_{50}$~25 µM) (Compound 31); 4-(4-{[(1,5-dimethyl-3-oxo-2-phenyl-2,3,dihydro-1H-pyrazol-4-yl) amino]sulfonyl}anilino)-4-oxo butanoic acid ($K_d$=2+/−1 µM) (Compound 4); 1,2-(3-methylthiotraizine),3,4-phenyl,6-[(2-methoxyphenoxy)Acetic Acid]morpholine ($K_d$<10 µM $IC_{50}$∞25 µM) (Compound 33); 4-{[2-(3,5-Dioxo-2,3,4,5-tetrahydro-[1,2,4]triazin-6-yl)-acetyl]-hydrazonomethyl}-benzoic acid ($K_d$<10 µM) (Compound 51); 2-(3-tert-Butylcarbamoyl-phenyl)-1,3-dioxo-2,3-dihydro-1H-isoindole-5-carboxylic acid ($K_d$~24 µM) (Compound 44); 5-{[2-(3-Methoxy-phenyl)-1,3-dioxo-2,3-dihydro-1H-isoindole-5-carbonyl]-amino}-isophthalic acid ($K_d$~12 µM) (Compound 45); 1-Ethyl-6-fluoro-7-[N'-(2-nitro-benzylidene)-hydrazino]-4-oxo-1,4-dihydro-quinoline-3-carboxylic acid ($K_d$<200 µM) (Compound 24); (3-benzoic)-1,3,dioxo-2,3-dihydro-1H-isoindole-5-sulfanyl-4-benzoic acid ($K_d$<200 µM) (Compound 38); and 2-[3-(3-Hydroxy-phenylcarbamoyl)-phenyl]-1,3-dioxo-2,3-dihydro-1H-isoindole-5-carboxylic acid ($K_d$<200 µM) (Compound 39).

Compounds that fluorescent (i.e., for Compounds 9, 31 and 33) were measured by a direct binding assay to S100B via fluorescence intensity changes. For those compounds that were not fluorescent (Compounds 1, 3, 4(pentamidine), 24, 38, 39, 44, 45 and 51), two approaches were used. First, changes in tyrosine fluorescence (for Tyr-17 of S100B) were sufficient in some cases to evaluate binding (Rustandi et al (1998), supra; and Szabo et al, FEBS Lett., 94:249-252 (1978)). However, to circumvent problems associated with the low quantum yield of the tyrosine residue, the F43W mutant of S100B was used (FIG. 12A), and then competition studies were done with wild-type S100B (FIG. 12B). In this S100B construct (in F43W S100B), the tryptophan residue is located in the target protein binding site, so the emission of the tryptophan mutant was measured in a straightforward manner at 338 nm as a function of adding compound. This F43W mutant has similar structure, $Ca^{2+}$-binding and target binding properties of wild-type S100B. Another approach was to bind a fluorescent probe to wild-type S100B and do competition binding assays with the compound. In this case, a fluorescent peptide derived from p53 (F385W) as the fluorescent probe ($K_D$=3.0 µM) or the TRTK-12 peptide ($K_D$=0.2 µM) were used as probes in the competition studies with compounds. Steady state experiments to determine binding constants were performed on Aminco Bowman Series 2 Luminescence Spectrophotofluorometer with the temperature of the cell (quartz cuvettes) maintained at 25° C. Two internal controls were performed in all titrations. EGTA was added to S100B to chelate the calcium and determine whether the interaction with the drug requires the $Ca^{2+}$-dependent conformational change observed for a number of protein targets (Weber et al, supra). In addition, the titrations were performed in the absence of calcium as a control. All compounds with fluorescence emission spectra were also routinely evaluated for photobleaching before proceeding. Buffers were also checked routinely for any contaminants that may fluoresce.

(b) Cellular Assays

The effect that compounds have on the growth of primary malignant melanoma cells (cell lines: C8146A and HTB 64) and normal melanocytes (Cell Applications Inc. 104-05 from neonatal foreskin) were measured. Pentamidine was found to inhibit the growth of malignant melanoma cells rather potently ($IC_{50}$=500 nM), with lesser effects on normal melanocytes (FIG. 13). The growth inhibition constants ($IC_{50}$ values) results from other compounds are listed above. In these studies, typically ~10,000 cells were distributed evenly across T25 vials. One day later, new media with or without the small molecule (2.5 µM or 25 µM) was added, and the cells were allowed to grow for an additional 13 days. Because some molecules were delivered in DMSO, the effect of DMSO (0.1-0.2% (v/v)) on cell growth was also checked and found to have no effect at these levels (FIG. 13). At this point, the cells were washed in phosphate buffer saline (PBS), harvested by treatment with trypsin, and placed in F10 media with 5.0% (v/v) fetal bovine serum (FBS), 5.0% (v/v) newborn calf serum (NCS), and 2.0% (w/v) penicillin/streptomycin. The cells were counted with a hemocytometer in quadruplicate trials.

(c) NMR Spectroscopy

NMR spectroscopy experiments were carried out to determine what amino acid residues of S100B and the small molecule are interacting (FIG. 14). Resonances of S100B that interact with the small molecules were identified by titrating compounds into holo-S100B and monitoring perturbations in chemical shifts of backbone amide-proton correlations in a $^{15}$N-edited HSQC spectrum (Mori et al, J. Magnetic Resonance, B108:94-98 (1995)). All of the small molecules tested were found to bind S100B in the p53 binding site (see FIG. 1 and FIG. 14) as determined by these HSQC chemical shift perturbation studies. An example of mapping the Compound-S100B interface is provided in FIGS. 14A-14C for the interaction between holo-S100B and Compound 4. As is the case with all of the compounds studied, Compound 4 interacts with the C-terminus of S100B (loop 4) and another region of S100B (loop 2) termed the "hinge". These residues are highlighted red in FIG. 14C for titrations with Compound 4. Resonance assignments of S100B bound to the small molecules were confirmed using a 3D NOESY-HSQC experiment, and the backbone and sidechain chemical shifts of $Ca^{+2}$-loaded S100B and S100B bound to p53 peptide as described by Drohat et al (1998), supra; Rustadni et al (2000), supra; and Rustadni et al (1998), supra, were also helpful in the assignment procedure. Regions of the inhibitors that interact with S100B were identified using epitope mapping via saturation transfer difference experiments (STDs) as described by Mayer et al, J. Am. Chem. Soc., 123:6108-6117 (2001). In FIG. 14A, protons of the compound that are proximal to S100B are indicated by arrows. To assign the STD both a 1D Watergate and a 2D TOCSY (MLEV pulse train with water suppression) were obtained.

All NMR spectra were acquired at 37° C. with a Bruker DMX600 NMR spectrometer (600.13 MHz for protons) equipped with four frequency channels and a triple resonance 3-axis gradient probe. In all cases, a 1 s relaxation delay was used, and quadrature detection in the indirect dimensions was obtained with States-TPPI phase cycling (Marion et al, Biochem., 28:6150-6156 (1989)).

Samples typically consisted of 100-300 µM S100B, 30 mM Tris (pH 6.5-7.4), 10 mM $CaCl_2$, 0.3 mM $NaN_3$, 0.4 mM EDTA, 5.0 mM DTT, 5.0% (v/v) $D_2O$ (pH 6.5). In cases where sample conditions needed to be changed, a control $Ca^{2+}$-S100B HSQC spectrum was collected. All NMR data were processed on computer workstations using the processing program nmrPipe (Delaglio et al, J. Biomol. NMR, 6:277-293 (1995)); and nmrView (Merck)). Time-domain data in the indirect dimensions were extended by no more than one-third using standard linear prediction routines (Zhu et al, J. Magnetic Resonance, 98:192-199 (1992)). All proton chemical shifts were reported with respect to the $H_2O$ or HDO signal taken as 4.658 ppm relative to external TSP (0.0 ppm)

at 37° C. The $^{15}$N chemical shifts were indirectly referenced using the following ratios of the zero-point frequencies at 37° C.: 0.10132905 for $^{15}$N to $^{1}$H (Spera et al, *J. Am. Chem. Soc.*, 113:5490-5492 (1991); Live et al, *J. Am. Chem. Soc.*, 106: 1939-1941 (1984); and Edison et al, *Methods Enzymol.*, 239: 3-79 (1994)).

(d) Structure-Based Modeling

Based on the binding of compounds listed above, HSQC NMR titrations, saturation transfer difference measurements (STDs), and NMR docking procedures, it was possible to identify regions of the various small molecules that would benefit from synthetic modification. Initially, pentamidine derivatives with a variable linker region were prepared (FIG. 15). This was possible because smaller STDs are detected between S100B and the pentamidine linker region. The optimal size linker (i.e., the linker that gives the most potent $IC_{50}$, $K_D$) was then used in straightforward syntheses of other "pentamidine"-like derivatives (see formulae (I) and (II) above and FIG. 15).

Likewise, docking methods were used to derive derivatives of other compounds that bind tightly to S100B ($K_D$<2 μM) including derivatives of Compound 3 and Compound 4.

For Compound 4, emphasis was given for obtaining compounds with less charge to facilitate entry into cancer cells.

(e) Summary

Because S100 proteins are up-regulated in numerous cancers, they are used clinically as a marker for tumor progression. It has been discovered herein that the calcium-dependent interaction of S100B with a tumor suppressor, p53, occurs in vivo and that this interaction inhibits p53 function. Thus, high levels of S100 proteins, such as S100B, contribute to uncontrolled cell growth in cells with elevated levels of S100B such as malignant melanoma. As a proof of principle, it has been shown that inhibiting the S100B-p53 interaction restores wild-type p53 function. Thus, small molecule analogues were developed to bind S100B and inhibit the p53 interaction with the goal of restoring p53 function. This was achieved, and several compounds were found that bind S100B, inhibit S100B-p53 complex formation, and reduce the growth rate of cancer cells by restoring p53 function (i.e., malignant melanoma). One of these compounds, pentamidine, is an FDA approved drug for another purpose, so this compound was characterized thoroughly.

Example 8

Model for S100B Regulation of p53 Function

A model for how S100B regulates p53 function is shown in FIG. 16. In its active form, each subunit of tetrameric p53 binds $Zn^{2+}$ and contain a sandwich of two antiparallel β-sheets that serve as a scaffold for a loop-sheet-helix DNA binding domain (Cho et al, *Science*, 265:346-355 (1994)). Upon binding specific DNA sequences (FIG. 16), p53 activates the transcription of downstream targets including a cyclin-dependent kinase inhibitor (p21$^{WAF/CIP1}$) cell cycle control proteins (cyclin G, GADD45), genes involved in apoptosis (i.e., Bax), and proteins, such as S100B and hdm2, which in turn negatively regulate p53 protein levels inside the cell via feedback control (Levine et al (1991), supra; Levine (1997), supra; and Freedman et al, supra). For S100B, the affinity of p53 for its promoter regions are relatively low (FIG. 8), which suggests that induction of S100B by p53 occurs only after higher affinity promoter sites are occupied (i.e., for GADD45, p21, etc.). For hdm2, p53 protein levels are down-regulated by an ubiquitin-mediated pathway, and the hdm2-p53 interaction is dependent on the phosphorylation state of p53 in the N-terminal transactivation domain (Schon et al, *J. Mol. Biol.*, 323:491-501 (2002)). Like hdm2, S100B also binds directly to p53 and contributes to lower p53 protein levels in cancer cells (FIGS. 1 and 4, and FIGS. 6A-6B). While the mechanism for how S100B contributes to lowering p53 levels inside cells is not yet established, it is believed to be related to its ability to dissociate the p53 tetramer (Baudier et al, supar) and/or cause conformational changes in the extreme C-terminus (Rustandi et al (1999); supra) and tetramerization domains of p53 (FIG. 16). Therefore, S100B is now the second known protein that is both (i) activated at the transcriptional level by p53 and (ii) then subsequently inhibits p53 function via feedback control (FIG. 16).

Another similarity between hdm2 (mdm2 in mice) and S100B is that the interactions of both proteins with p53 are regulated by phosphorylation (Rustandi et al (2000), supra; Schon et al, supra; Wilder et al, supra; and Buschmann et al, *Cancer Res.*, 60:896-900 (2000)). For mdm2, phosphorylation of one residue (T18) in p53 inhibits mdm2 binding (>10-fold), which then protects p53 from mdm2/ubiquitin-dependent degradation (Schon et al, supra; and Piette et al, *Oncogene*, 15:1001-1010 (1997)). Similarly, phosphorylation and acetylation in the C-terminus of p53 can protect the tumor suppressor from interactions with S100B (Rustandi et al (2000), supra; and Youmell et al, *Biochem. Biophys. Res. Commun.*, 245:514-518 (1998)). Also striking, is that the 3D structure of the N-terminal domain of mdm2 resembles S100B and other EF-hand binding proteins such as calmodulin, despite the fact that it does not bind calcium (Milner-White, *J. Mol. Biol.*, 286:957-963 (1999)). Like S100 proteins, mdm2 forms heterodimers with a structural homologue (mdmX), which regulates its own oncogenic activity (Stad et al, *EMBO Rep.*, 2:1029-1034 (2001)). In its most active form, p53 is a tetramer held in the C-terminal region as a dimer of dimers to form an X-type four-helix bundle (Jeffrey et al, *Science*, 267:1498-1502 (1995); Lee et al, *Nat. Struct. Biol.*, 1:877-890 (1994); and Clore et al, *Science*, 265:386-391 (1994)). Directly C-terminal to the tetramer domain is a basic region termed the "extreme C-terminus" or the "C-terminal negative regulatory domain". Thus, an important distinction between these proteins (hdm2 vs. S100B) is that the S100B interaction with the C-terminus of p53 is $Ca^{2+}$-dependent (Rustandi et al (1998), supra; and Baudier et al, supra) and can link p53 biology to calcium-mediated signaling pathways and extracellular growth responses (FIG. 17); whereas, hdm2 binds the N-terminus of p53 in a calcium-independent manner (Momand et al, supra; and Prives, *Cell*, 95:5-8 (1998)).

The interaction between S100B and p53 occurs in a cell-cycle dependent manner (i.e., during $G_1$; FIG. 5B) in addition to being regulated by phosphorylation and calcium levels inside the cell. This finding is significant since the $G_1$ phase precedes DNA synthesis and constitutes an important checkpoint for p53 in response to DNA damage. The p53 $G_1$ checkpoint is mediated by the cyclin dependent kinase inhibitor p21, one of the p53 downstream effector genes (Appella et al, supra; Prives et al (1999), supra; and Vousden, supra). This inhibitor prevents phosphorylation of pRb and arrests cells in $G_1$ in response to DNA damage. It is believed that this arrest in $G_1$ allows cells time to repair their DNA and prevents the transmission of damaged DNA to daughter cells (Prives et al (1999), supra; and Vousden, supra). It has previously been shown that S100B prevents up-regulation of p21 by p53 (Lin et al, supra), so arrest of the cell cycle is diminished in its presence and the cell cycle proceeds unregulated. Furthermore, the interaction between S100B and p53 during $G_1$ could prevent the entry of p53 to the nucleus during S and further inhibit p53 transcriptional activity. Thus, the overall effect of S100B on wild-type p53 could mimic cellular aberrations, such as gene amplification and mutations that are encountered with non-functional mutants of p53.

While it is not completely clear how cancer progresses when wild-type p53 is present, one possible explanation for this paradigm is that elevated levels of proteins that negatively regulate p53, such as S100B, are responsible. An example of a cancer with wild-type p53 and high levels of S100B is malignant melanoma. Interestingly, S100 calcium-binding proteins, such as S100B, are elevated in these cells and are used as a marker for skin cancer (Cochran et al, *Melanoma Res.*, 3:325-330 (1993); Boni et al, supra; and Marks et al, *Exp. Cell Res.*, 187:59-64 (1990)). In addition, wild-type p53 protein levels are relatively low in malignant melanoma when compared to cells without S100 protein (FIGS. 2A-2B). For primary skin cancer cells, it has been shown in the present invention that there is a direct interaction between p53 and S100B during $G_1$ of the cell-cycle and that wild-type p53 levels can be restored upon the addition of RNA that is antisense to that of S100B (FIG. 9). This result directly implicates S100B in the down-regulation of wild-type p53 in vivo and is consistent with large decreases in p53 protein levels observed previously in transient co-transfections of p53 and S100B (Lin et al, supra). With these results in mind, a small molecule inhibitor that blocks the S100B-p53 interaction and restores wild-type p53 to more normal levels is believed to be useful as a therapeutic agent for the treatment of cancers, such as malignant melanoma.

While the invention has been described in detail and with reference to specific embodiments thereof, it will be apparent to one skilled in the art that various changes and modifications can be made therein without departing from the spirit and scope thereof.

What is claimed is:

1. A method of activating p53 in astrocytoma cells, consisting of administering pentamidine isethionate or pentamidine to said astrocytoma cells which express S100 and p53.

2. The method of claim 1, wherein said S100 is S100B.

3. The method of claim 1, wherein said compound is pentamidine.

4. A method of inhibiting binding of S100 to p53 in astrocytoma cells, consisting of administering pentamidine isethionate or pentamidine to said astrocytoma cells which express S100 and p53.

5. The method of claim 4, wherein said S100 is S100B.

6. A method of inhibiting binding of S100 to p53 in astrocytoma cells, consisting of administering pentamidine to said astrocytoma cells which express S100 and p53.

* * * * *

UNITED STATES PATENT AND TRADEMARK OFFICE
CERTIFICATE OF CORRECTION

PATENT NO. : 8,053,477 B2  Page 1 of 1
APPLICATION NO. : 10/397239
DATED : November 8, 2011
INVENTOR(S) : David Weber et al.

It is certified that error appears in the above-identified patent and that said Letters Patent is hereby corrected as shown below:

Column 1, lines 14-18 please delete: "The work described herein was supported by grants from the NIH (grant numbers MG58888, NSO43916 and GM052071) and from the American Cancer Society (RPG0004001-CCG). The Federal Government has certain rights in this invention."

and insert therefor: -- This invention was made with government support under Grant Numbers GM052071, GM058888, and NS043916 awarded by the National Institutes of Health. The government has certain rights in the invention --

Signed and Sealed this
Twenty-first Day of February, 2012

David J. Kappos
*Director of the United States Patent and Trademark Office*